(12) United States Patent
Nishide et al.

(10) Patent No.: US 8,859,112 B2
(45) Date of Patent: Oct. 14, 2014

(54) ORGANIC COMPOUND AND ORGANIC LIGHT EMITTING ELEMENT USING THE SAME

(75) Inventors: Yosuke Nishide, Kawasaki (JP); Taiki Watanabe, Akishima (JP); Tetsuya Kosuge, Yokohama (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 222 days.

(21) Appl. No.: 13/595,050

(22) Filed: Aug. 27, 2012

(65) Prior Publication Data
US 2013/0049581 A1 Feb. 28, 2013

(30) Foreign Application Priority Data

Aug. 30, 2011 (JP) ................. 2011-187169

(51) Int. Cl.
| | | |
|---|---|---|
| C07C 13/72 | (2006.01) | |
| H01L 51/54 | (2006.01) | |
| H01L 51/00 | (2006.01) | |
| C07C 13/62 | (2006.01) | |
| C09K 11/06 | (2006.01) | |
| H01L 51/50 | (2006.01) | |

(52) U.S. Cl.
CPC ........ *H01L 51/0056* (2013.01); *C07C 2103/94* (2013.01); *C07C 13/62* (2013.01); *C09K 11/06* (2013.01); *C09K 2211/1011* (2013.01); *H01L 51/006* (2013.01); *H01L 51/5012* (2013.01); *H01L 2251/308* (2013.01); *H01L 51/0072* (2013.01); *C07C 2103/90* (2013.01); *C07C 13/72* (2013.01); *Y10S 428/917* (2013.01)
USPC ........... 428/690; 428/917; 313/504; 313/506; 585/27

(58) Field of Classification Search
CPC ........... C09K 11/06; C09K 2211/1011; H01L 51/0056; H01L 51/5012; H01L 51/006; H01L 2251/308; H01L 51/0072; C07C 13/62; C07C 13/72; C07C 2103/94; C07C 2103/90
See application file for complete search history.

(56) References Cited

FOREIGN PATENT DOCUMENTS

JP 2003-272866 A 9/2003

*Primary Examiner* — Dawn L. Garrett
(74) *Attorney, Agent, or Firm* — Canon U.S.A., Inc., IP Division

(57) ABSTRACT

An organic compound represented by the following general formula [1] is provided. In the general formula [1], $R_1$ to $R_3$ are each independently selected from the group consisting of a hydrogen atom, a fluorine group, an alkyl group having 1 to 4 carbon atoms, and an aryl group, the aryl group is a phenyl group, a biphenyl group, or a terphenyl group, the aryl group may further include an alkyl group having 1 to 4 carbon atoms and/or a fluorine group as a substituent, and $R_4$ to $R_{17}$ are each independently selected from the group consisting of a hydrogen atom, an alkyl group having 1 to 4 carbon atoms, and a fluorine group.

[1]

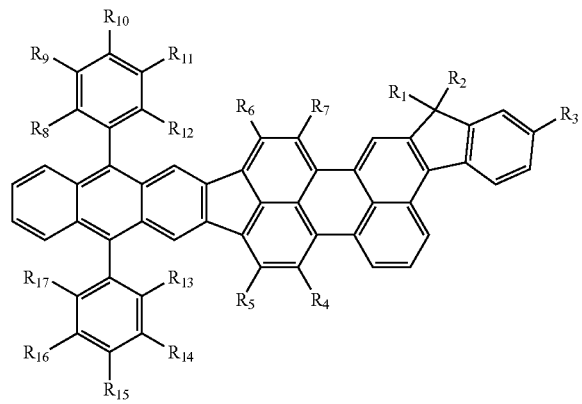

11 Claims, 3 Drawing Sheets

BASIC SKELETON OF A1

BASIC SKELETON OF C1

BASIC SKELETON OF a-1 AND a-2

A1 a-2 a-3

BASIC SKELETON OF A1

BASIC SKELETON OF C1

BASIC SKELETON OF a-1 AND a-2

ORGANIC COMPOUND AND ORGANIC LIGHT EMITTING ELEMENT USING THE SAME

BACKGROUND OF THE INVENTION

1. Field of the Invention

The present invention relates to a novel organic compound and an organic light emitting element including the same.

2. Description of the Related Art

An organic light emitting element is an element including a pair of electrodes and an organic compound layer arranged therebetween. When an electron and a hole are injected from the pair of electrodes, an exciton is generated in a light emitting organic compound of the organic compound layer, and light is emitted when the exciton returns to the ground state.

The organic light emitting element is also called an organic electroluminescent element or an organic EL element.

The recent advances in the organic light emitting element are remarkable, and a high-speed response, thin, and light-weight light emitting device which can be driven at a low voltage and which has various light emitting wavelengths can be formed.

Heretofore, creation of novel red light emitting organic compounds has been energetically carried out. The reason for this is that in order to provide an organic light emitting element having a higher color purity and a higher efficiency, it is believed that the above compounds must be created.

Japanese Patent Laid-Open No. 2003-272866 has disclosed a condensed polycyclic compound (a-1) as a red light emitting material.

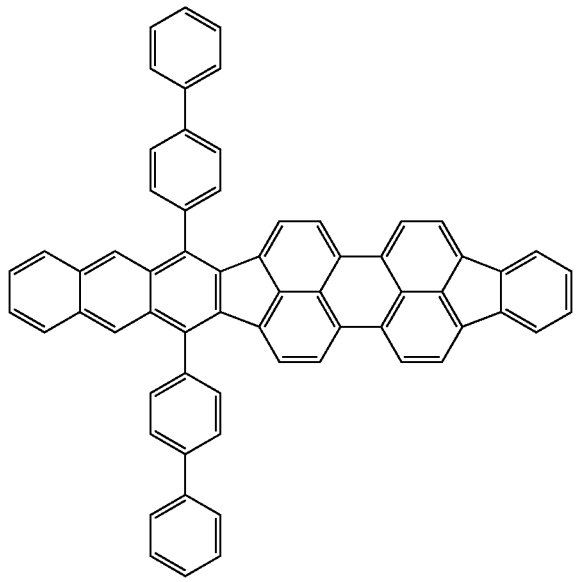

a-1

However, although the condensed polycyclic compound a-1 emits light in a red spectrum region, the light emitting efficiency and the color purity thereof are not satisfactory.

SUMMARY OF THE INVENTION

Aspects of the present invention provide a novel condensed polycyclic compound which emits red light and which has a high hole injection property. In addition, aspects of the present invention also provide an organic red light emitting element which includes the above condensed polycyclic compound and which has a high efficiency and a high color purity. The novel compound according to aspects of the present invention is a novel organic compound represented by the following general formula [1].

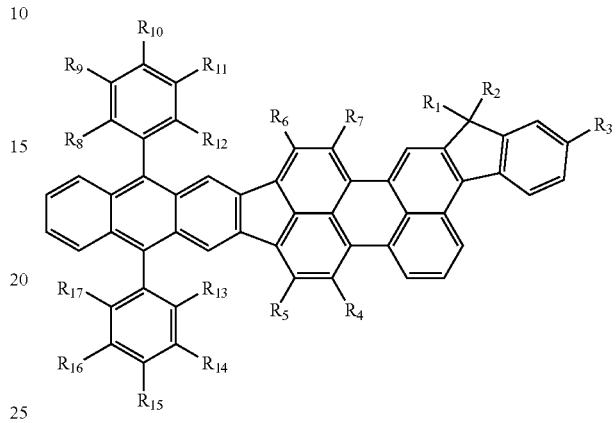

[1]

In the general formula [1], $R_1$ to $R_3$ are each independently selected from the group consisting of a hydrogen atom, a fluorine group, an alkyl group having 1 to 4 carbon atoms, and an aryl group.

The aryl group is a phenyl group, a biphenyl group, or a terphenyl group.

The aryl group may further include an alkyl group having 1 to 4 carbon atoms and/or a fluorine group as a substituent. $R_4$ to $R_{17}$ are each independently selected from the group consisting of a hydrogen atom, an alkyl group having 1 to 4 carbon atoms, and a fluorine group.

In addition, a compound having the structure represented by the following general formula [2] in which $R_1$ and $R_2$ are bonded to each other to form a ring is also included in the above novel compound. However, in the general formula [2], $R_{18}$ and $R_{19}$ are each independently selected from the group consisting of a hydrogen atom, a fluorine group, and a t-butyl group.

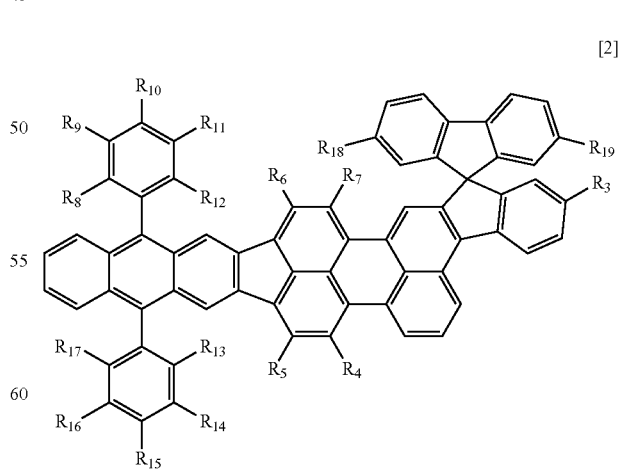

[2]

According to aspects of the present invention, a novel condensed polycyclic compound which emits red light and which has a high hole injection property can be provided. In addition, an organic red light emitting element which includes the above novel compound and which has a high efficiency and a high color purity can also be provided.

Further features of the present invention will become apparent from the following description of exemplary embodiments with reference to the attached drawings.

DESCRIPTION OF THE EMBODIMENTS

Aspects of the present invention provide a novel organic compound represented by the following general formula [1].

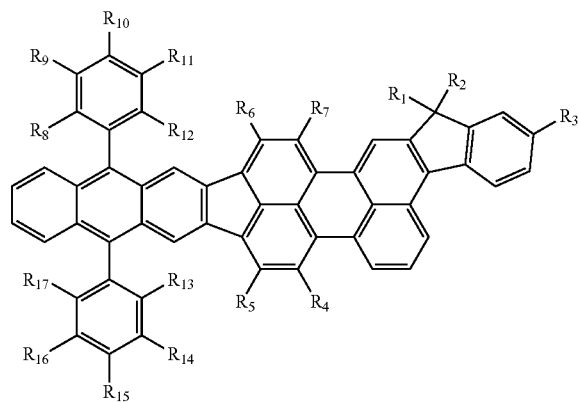

[1]

In the general formula [1], $R_1$ to $R_3$ are each independently selected from the group consisting of a hydrogen atom, a fluorine group, an alkyl group having 1 to 4 carbon atoms, and an aryl group.

The aryl group is a phenyl group, a biphenyl group, or a terphenyl group.

The aryl group may further include an alkyl group having 1 to 4 carbon atoms and/or a fluorine group as a substituent. $R_4$ to $R_{17}$ are each independently selected from the group consisting of a hydrogen group, an alkyl group having 1 to 4 carbon atoms, and a fluorine group.

In addition, a compound having the structure represented by the following general formula [2] in which $R_1$ and $R_2$ are bonded to each other to form a ring is also included in the above novel compound. However, in the general formula [2], $R_{18}$ and $R_{19}$ are each independently selected from the group consisting of a hydrogen atom, a fluorine group, and a t-butyl group.

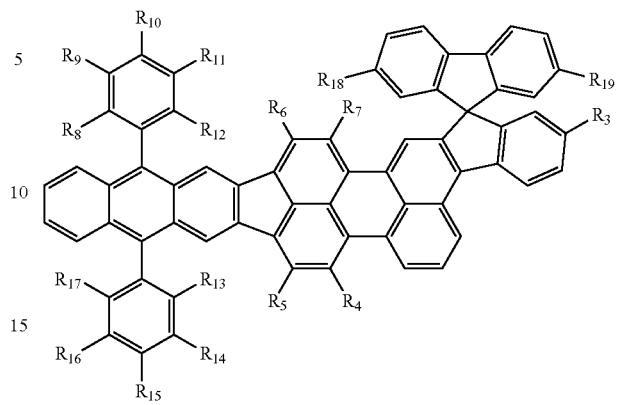

[2]

In particular, the alkyl group having 1 to 4 carbon atoms represented by each of $R_1$ to $R_{17}$ in the general formula [1] is a methyl group, an ethyl group, a propyl group, an iso-propyl group, or a t-butyl group.

The alkyl group having 1 to 4 carbon atoms which the aryl group may further include as a substituent is particularly a methyl group, an ethyl group, a propyl group, an iso-propyl group, or a t-butyl group.

The novel condensed polycyclic compound according to aspects of the present invention represented by the general formula [1] emits red light, and the HOMO level thereof is high (closer to the vacuum level). Hence, when the compound according to aspects of the present invention is used as a light emitting material of an organic light emitting element, the hole injection property (or hole trapping property) is improved, and the light emitting efficiency is increased.

Hence, when the compound according to aspects of the present invention is used, an organic red light emitting element having a high efficiency and a high color purity can be provided.

(Comparison between Example Compound (A1) According to Aspects of the Present Invention and Condensed Polycyclic Compound (a-2))

Figure 1:
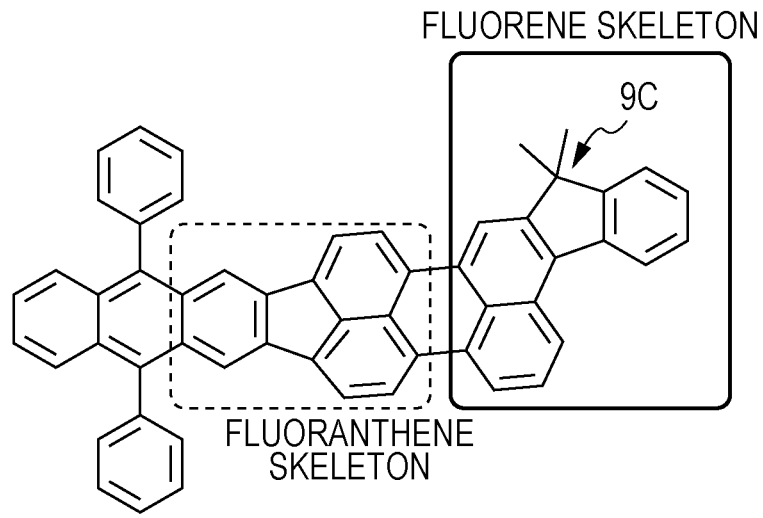
FIG. 1 shows an example compound (A1) according to aspects of the present invention and condensed polycyclic compounds (a-2) and (a-3) for comparison therebetween.
Figure 1:
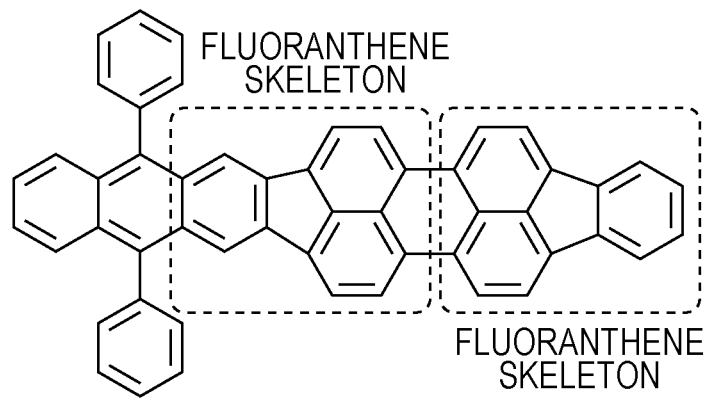
Figure 1:
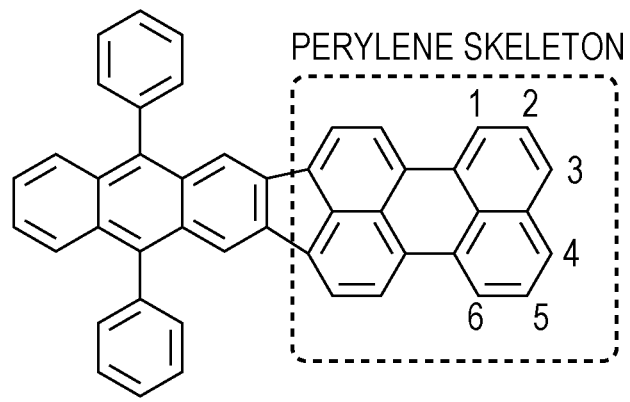
Figure 2:
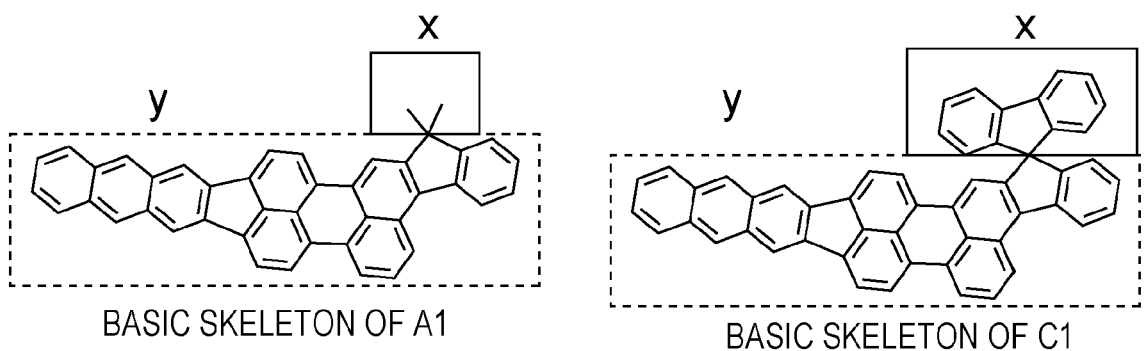
FIG. 2 shows the example compound (A1) according to aspects of the present invention and the condensed polycyclic compounds (a-1) and (a-2) for comparison therebetween.
Figure 2:
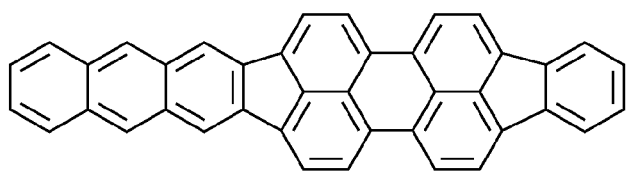

With reference to FIGS. 1 and 2, the example compound (A1) according to aspects of the present invention and compounds (a-2) and (a-3), each of which is an analogue of the condensed polycyclic compound (a-1) disclosed in Japanese Patent Laid-Open No. 2003-272866, will be described for comparison purpose. In the above patent document, a compound (such as the condensed polycyclic compound (a-2)) has been disclosed as an example compound in which the condensed polycyclic compound (a-3) is used as a basic skeleton and in which aromatic rings are condensed at 3- and 4-substitution positions to form a fluoranthene skeleton.

When the emission spectrum of the condensed polycyclic compound (a-3) was measured by a method similar to that described in Example 1, the peak wavelength was 550 nm, and yellow light emission was observed. The example compound (A1) according to aspects of the present invention and the condensed polycyclic compound (a-2) both emit light in a red spectrum region. The reason for this is that these compounds each have a molecular structure in which conjugation is further expanded from that of a perylene skeleton. In addition, the light emission in a red spectrum region in aspects of the present invention indicates that the peak wavelength of the emission spectrum in a toluene diluted solution is in a range of 580 to 630 nm.

However, the properties of the example compound (A1) according to aspects of the present invention are significantly different from those of the condensed polycyclic compound (a-2). That is, the example compound (A1) according to aspects of the present invention has high hole and electron injection properties, and on the other hand, the condensed polycyclic compound (a-2) has a low hole injection property.

In general, a condensed polycyclic compound having a five-membered ring in its molecule, such as a fluoranthene skeleton, is likely to receive an electron due to its electron deficiency. This indicates that the LUMO level is lowered (apart from the vacuum level) and that the electron injection property is enhanced. On the other hand, a compound having a skeleton, such as a fluorene skeleton, which includes a non-aromatic five-membered ring in its molecule is electron rich and is likely to receive a hole. This indicates that the HOMO level becomes higher (closer to the vacuum level) and that the hole injection property is enhanced.

In addition, when the example compound (A1) is used for a guest material of a light emitting layer, the hole and electron injection properties are enhanced, and the carriers can be efficiently confined in the light emitting layer. That is, when the example compound (A1) having high hole and electron injection properties is used, an organic light emitting element which achieves a decrease in drive voltage and an improvement in efficiency can be obtained. Furthermore, it was found that when the molecular orbital calculation was performed, the calculated value of the HOMO level also supported that described above.

The calculated HOMO levels of the respective compounds are shown in Table 1.

In this embodiment, the molecular orbital calculation was performed by the following quantum chemical calculation method.

The phenomenon in which the HOMO level becomes higher indicates that the HOMO level becomes closer to the vacuum level, that is, in other words, that the value of the HOMO level is increased.

In the molecular orbital calculation, the S1 energy (lowest excited singlet state energy), the HOMO level, and the LUMO level were obtained by the following method.

The above molecular orbital calculation was performed by a DFT calculation method at the 6-31+G(d) basic function using currently widely used Gaussian 03 (Gaussian 03, Revision D. 01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M.

TABLE 1

| COMPOUND | MOLECULAR STRUCTURAL FORMULA | HOMO (eV) |
| --- | --- | --- |
| A1 | 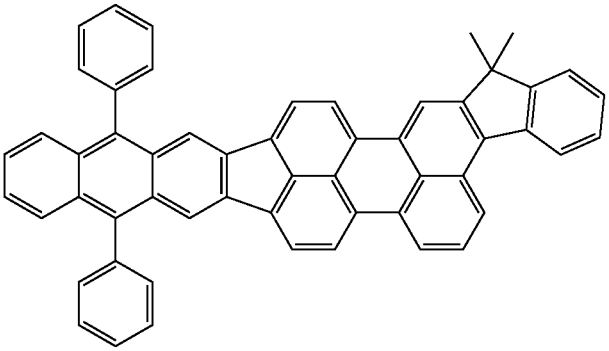 [SMILES: CC1(C)c2ccccc2-c2c1cc1c3ccc4c5c(ccc(c6cccc2c61)c53)-c1cc2c(-c3ccccc3)c3ccccc3c(-c3ccccc3)c2cc1-4] | −4.62 |
| a-2 | 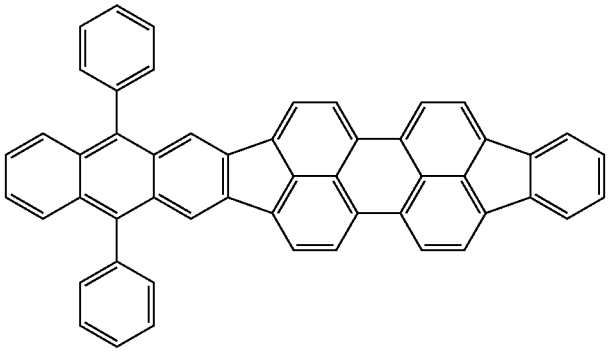 [SMILES: c1ccc(-c2c3ccccc3c(-c3ccccc3)c3cc4c(cc23)-c2ccc3c5ccc6c7c(ccc(c8ccc-4c2c38)c75)-c2ccccc2-6)cc1] | −4.77 |

W. Gill, B. Johnson, W. Chen, M. W. Wong, C. Gonzalez, and J. A. Pople, Gaussian, Inc., Wallingford Conn., 2004).

Hence, compared to the condensed polycyclic compound (a-2) having only an electron accepting portion, by the example compound (A1) according to aspects of the present invention having both a hole accepting portion and an electron accepting portion in its molecule, an organic light emitting element which achieves a decrease in drive voltage and an improvement in efficiency can be obtained.

In this embodiment, although the example compound (A1) according to aspects of the present invention has been described by way of example for the comparison purpose, the above properties can also be applied to all the novel condensed polycyclic compounds according to aspects of the present invention.

In addition, as another feature of the basic skeleton of the compound according to aspects of the present invention, when a substituent is substituted at the 9C-position of the fluorene portion, the bulk of the compound is stereochemically increased. As shown by the molecular structural formula of the basis skeleton of the compound (A1) in FIG. 2, since an x plane and a y plane are arranged orthogonal to each other through the 9C-position of the fluorene portion, the intermolecular stack can be further reduced. In addition, as shown in FIG. 2, since the steric hindrance group of the basic skeleton of a compound (C1) is larger than that of the basic skeleton of the compound (A1), the intermolecular stack can be further suppressed. As a result, when the compound (C1) is used as a light emitting material of an organic light emitting element, an energy loss between molecules is reduced in an excited state, and a highly efficient light emission can be obtained.

On the other hand, as shown in FIG. 2, the basic skeletons of the condensed polycyclic compounds (a-1) and (a-2) are each strongly influenced by the intermolecular stack because of its high planarity.

When the example compound (A1) according to aspects of the present invention is used as a light emitting material of an organic light emitting element, the concentration quenching can be reduced as compared to that obtained by the condensed polycyclic compounds (a-1) and (a-2), and as a result, a higher efficient light emission can be obtained.

In addition, the properties described above can also be applied to all the novel organic compounds according to aspects of the present invention.

The novel organic compound according to aspects of the present invention can be used for a light emitting layer of an organic light emitting element.

The novel compound according to aspects of the present invention can be used as a gust material of the light emitting layer. The guest material may also be called a dopant material. In this embodiment, a host material is a material having the highest weight ratio in the light emitting layer, and the guest material is a material which has a weight ratio lower than that of the host material and which is responsible for primary light emission.

In one case, the novel compound according to aspects of the present invention may be used as a gust material which emits red light. An organic light emitting element using this guest material may be either a red light emitting element or a white light emitting element.

(Examples of Organic Compound According to Aspects of the Present Invention)

Particular examples of the compound represented by the general formula [1] will be shown below. However, the present invention is not limited thereto.

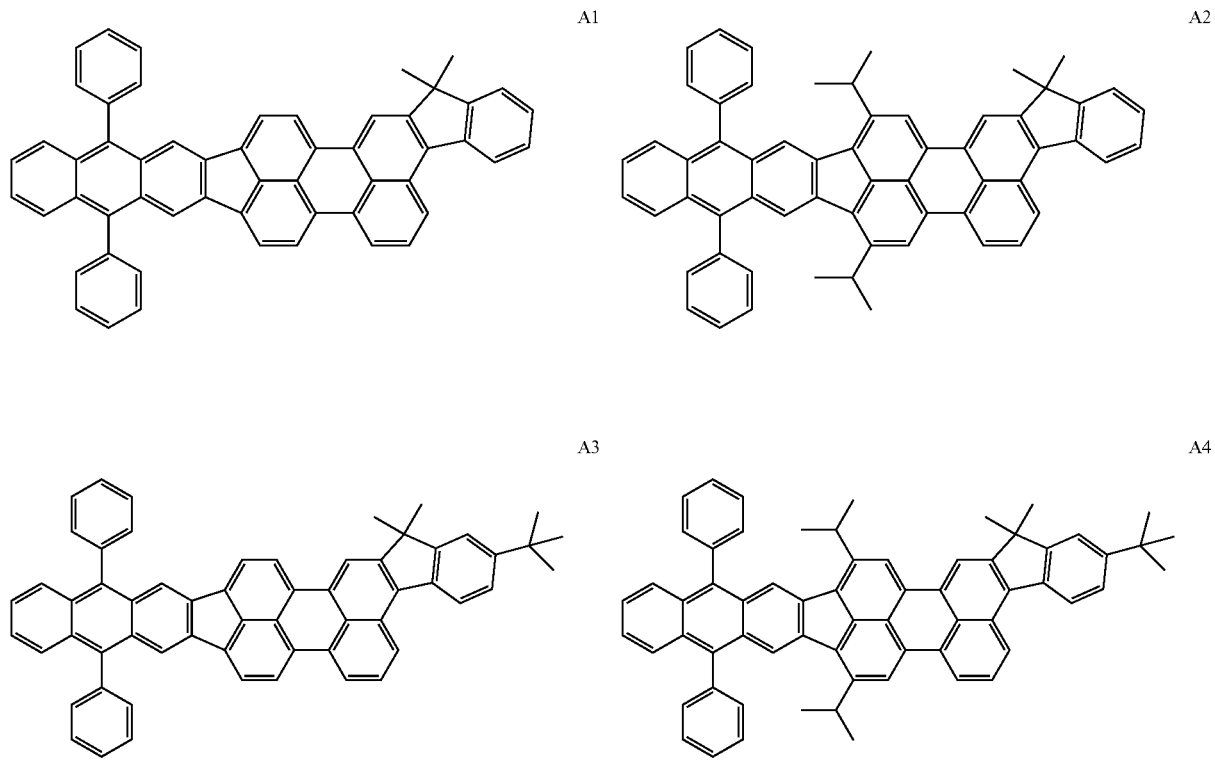

-continued
A5
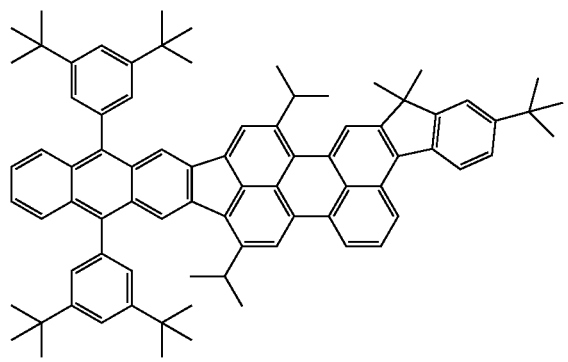
A6
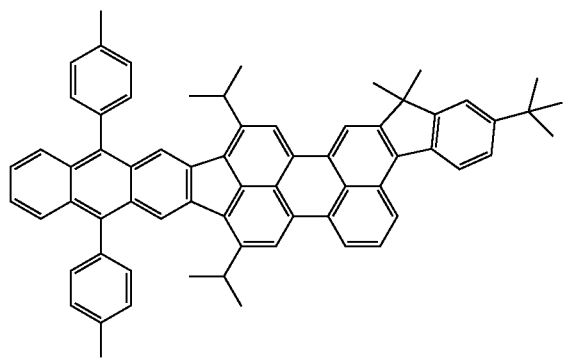
A7
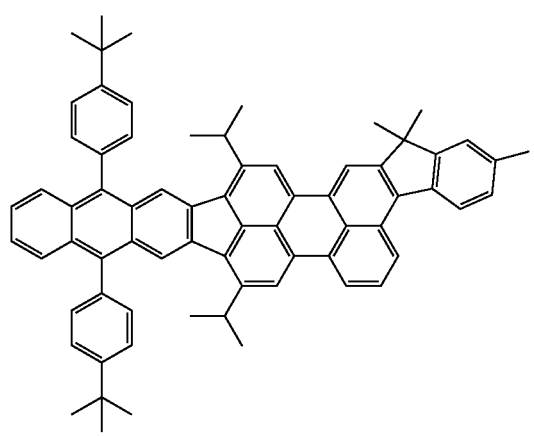
A8
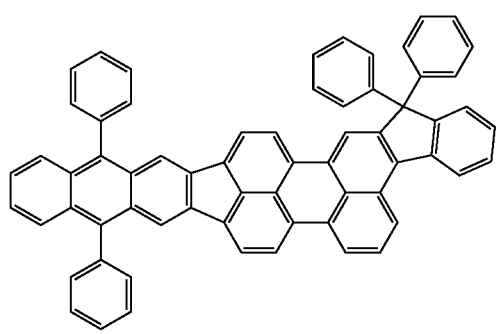
B1
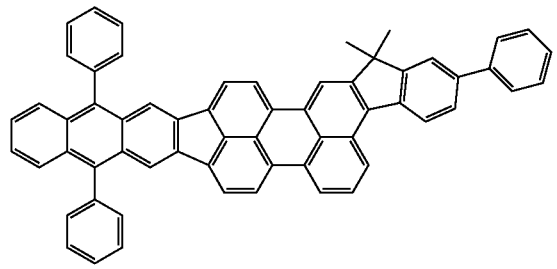
B2
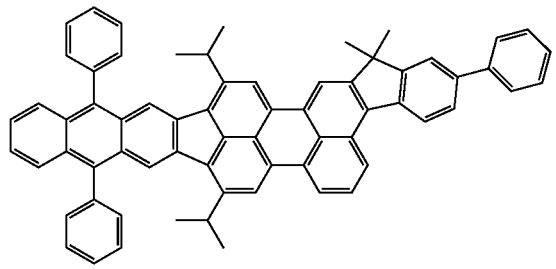
B3
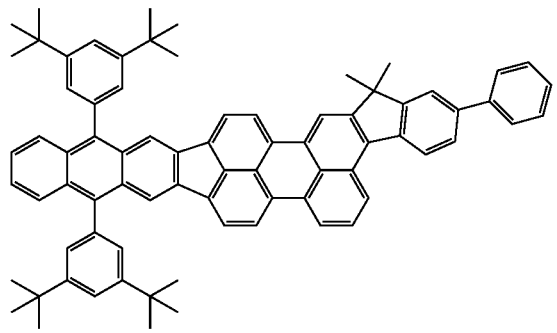
B4
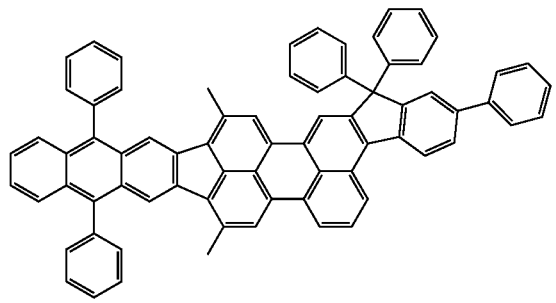

-continued
B5
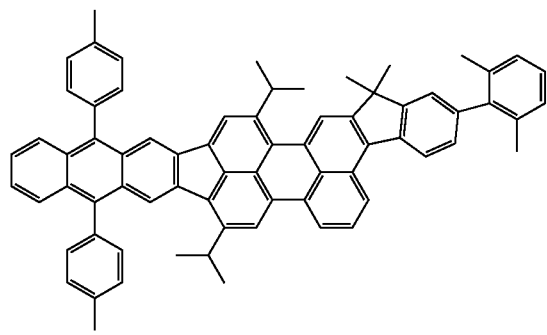
B6
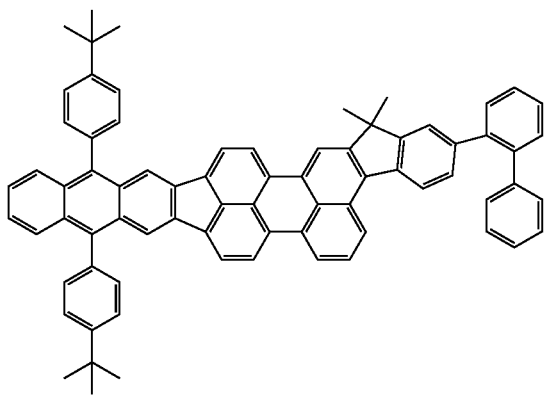
B7
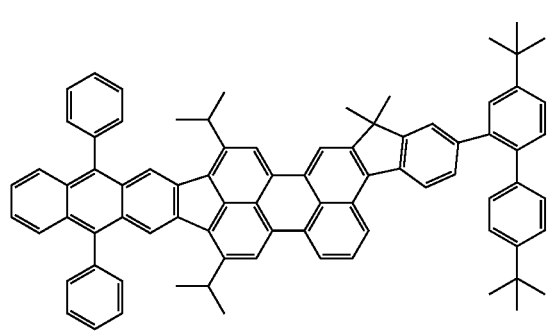
B8
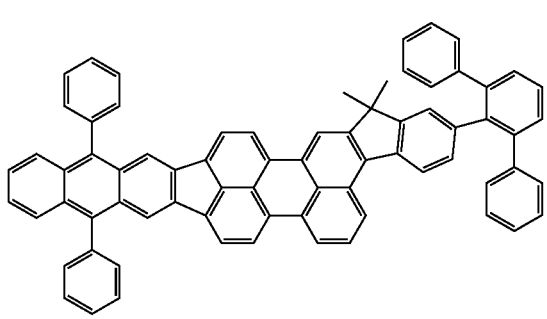
C1
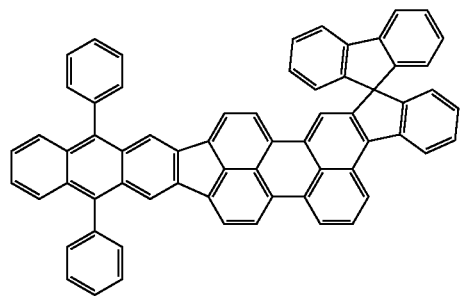
C2
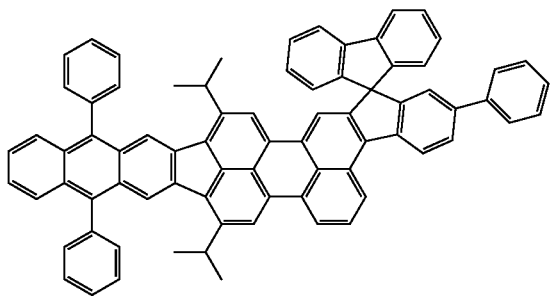
C3
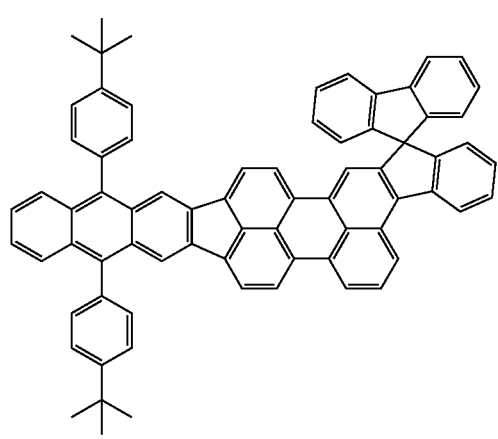
C4
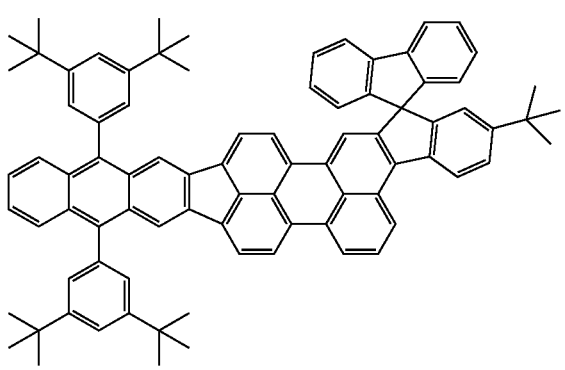

-continued
C5
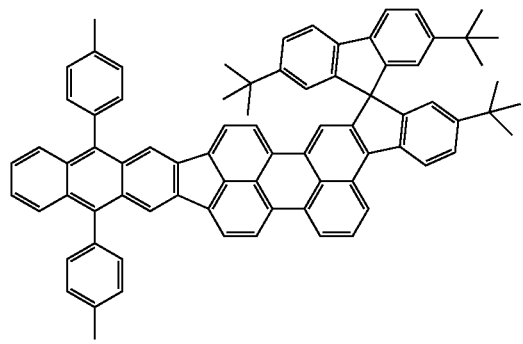
C6
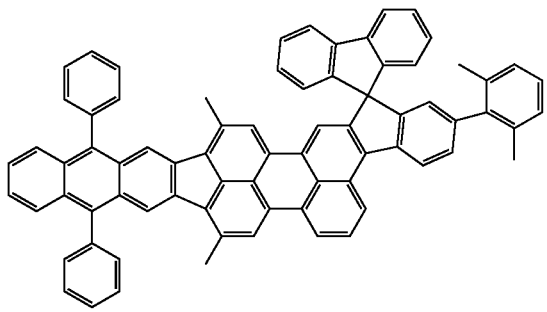
C7
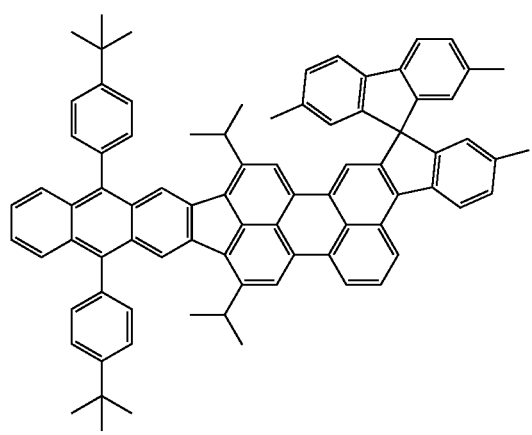
C8
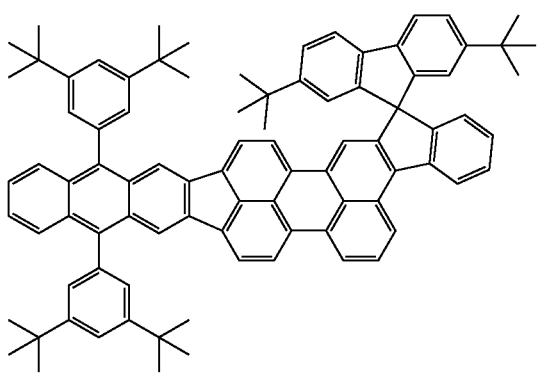
D1
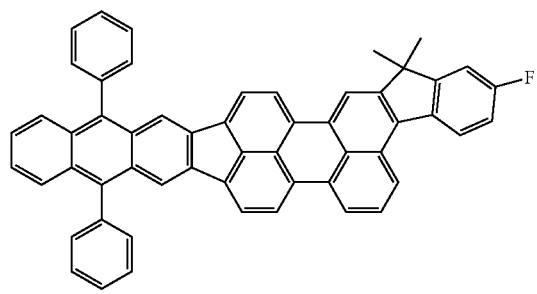
D2
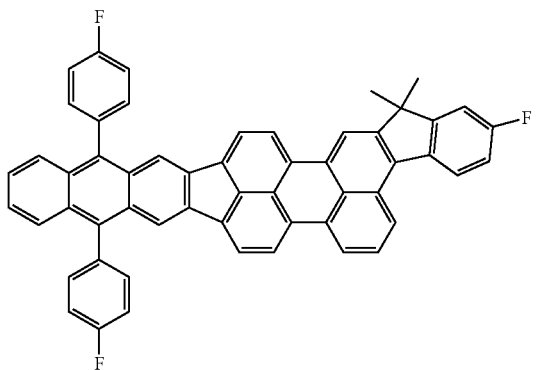
D3
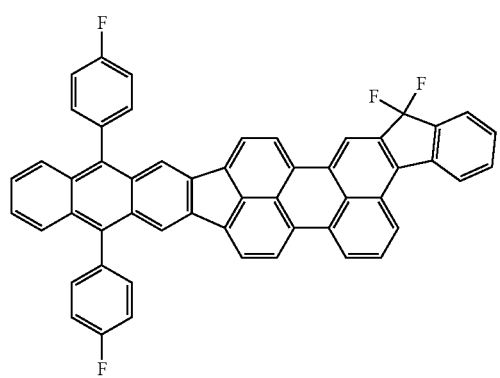
D4
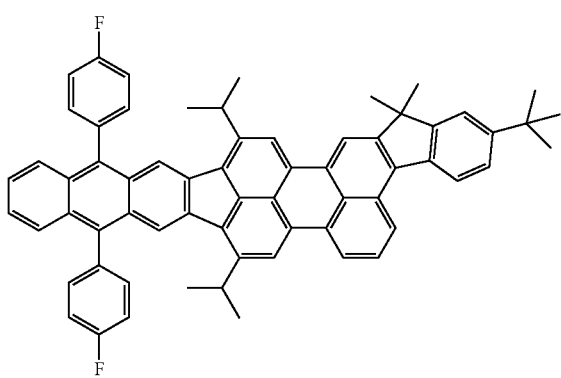

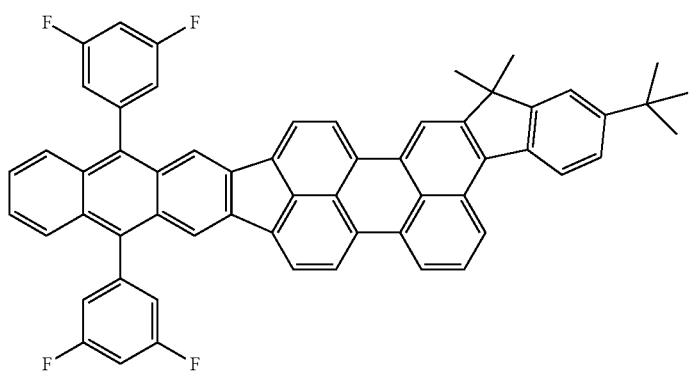

D5

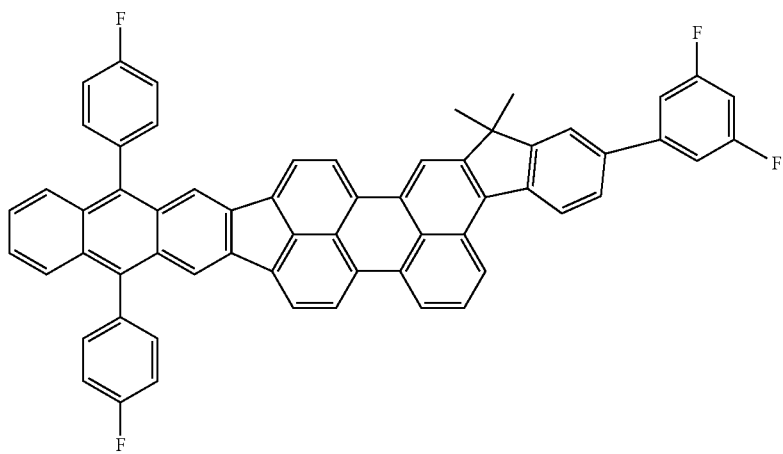

D6

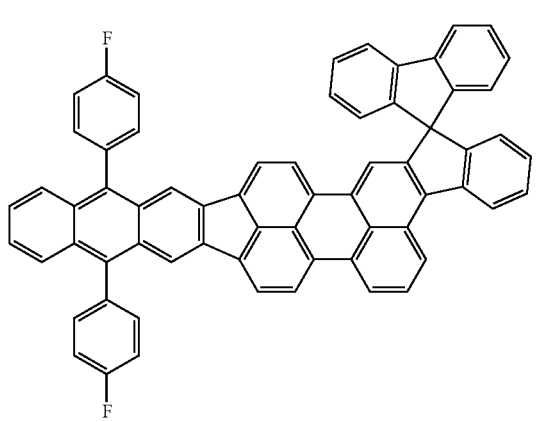

D7

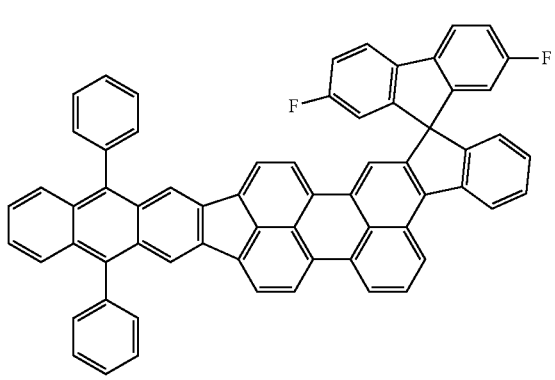

D8

(Properties of Example Compounds)

Examples of the novel organic compounds represented by the general formula [1] are shown in a group A to a group D.

On all the compounds in the group A to the group D, an alkyl group having 1 to 4 carbon atoms, an aryl group, such as a phenyl group, a biphenyl group, or a terphenyl group, and/or a fluorine group is substituted. The purpose of this substitution is to suppress the stack and to perform fine adjustment of the emission wavelength. Besides the improvement in color purity, the fine adjustment of the emission wavelength also plays an important role when an organic light emitting element is used in combination with a color filter.

The compounds in the group A to the group C are each formed of carbon atoms and hydrogen atoms and have high heat stability and electrochemical stability. When being driven, an organic light emitting element is placed in a harsh environment in which, for example, Joule heat is generated in the element, and an organic compound is repeatedly oxidized and reduced; hence, the above stabilities are important properties.

The group A is a compound group in which in the compound represented by the general formula [1], a hydrogen atom or an alkyl group having 1 to 4 carbon atoms is substituted at $R_3$. Hence, among the compounds according to aspects of the present invention, the compounds in this group each have a relatively low molecular weight and a low sublimation temperature. As for the emission wavelength, among the compounds according to aspects of the present invention, the compounds in this group each have an emission wavelength at a relatively short wavelength side. Of course, the short wavelength side indicates a short wavelength side in a red spectrum region.

The group B is a compound group in which in the compound represented by the general formula [1], a phenyl group, a biphenyl group, or a terphenyl group is substituted at $R_3$. When an aryl group is substituted at the substitution position $R_3$, light emission at a long wavelength side is obtained. Hence, among the compounds according to aspects of the present invention, the compounds in this group each have an emission wavelength at a relatively long wavelength side. Of course, the long wavelength side indicates a long wavelength side in a red spectrum region.

The group C is a compound group in which in the compound represented by the general formula [1], $R_1$ and $R_2$ each indicate a phenyl group, and these phenyl groups are further bonded to each other to form a spiro skeleton. In a partial structure having a spiro fluorene skeleton, since a fluorene portion is arranged orthogonal to a basic skeleton plane, among the compounds in the group A to the group C according to aspects of the present invention, the molecular stack can be further reduced. In addition, since the spiro structure is formed by the two cyclic compounds which are bonded to each other through one sp3 carbon, this structure is stiff, that is, the molecular oscillation is suppressed in this structure. Hence, among the compounds according to aspects of the present invention, the compounds in this group each have higher heat stability.

The compound group D is a compound group in which in the general formula [1], a fluorine group is substituted at least one of $R_1$ to $R_{17}$. When a fluorine group is introduced, it is expected that the intermolecular stack can be reduced. The reason for this is that since a fluorine atom has a significantly high electronegativity and is greatly polarized in its molecule, the distance between molecules is increased due to the electric repulsion of fluorine atoms. In addition, a fluorine group has a small molecular weight as compared to that of an alkyl group and an aryl group, each of which reduces the intermolecular stack. Hence, the sublimation temperature can also be decreased. Accordingly, among the compounds according to aspects of the present invention, the compounds in the group D each have a significant effect of reducing the intermolecular stack and also have a low sublimation temperature.

The calculated values of S1 of the example compounds according to aspects of the present invention and the measured value thereof described in Examples are shown in Table 2. In this embodiment, S1 is shown by the equivalent wavelength value. As described above, the light emission in a red spectrum region in aspects of the present invention indicates that the peak wavelength of the emission spectrum in a toluene diluted solution is in a range of 580 to 630 nm. In addition, the light emission may be in a region in which the peak wavelength of the emission spectrum in a toluene diluted solution is in a range of 585 to 610 nm. When light is emitted in this region, red light emission having a high color purity and a high efficiency can be obtained.

In one case of a red spectrum region, the compounds in the group A each emit light at a relatively short wavelength side.
In another case of a red spectrum region, the compounds in the group B each emit light at a relatively long wavelength side.
In another case of a red spectrum region, the compounds in the group C each emit light in an intermediate wavelength range.
In a red spectrum region, the compounds in the group D are each able to adjust the emission wavelength in a relatively wide wavelength range. The reason for this is that the emission wavelength is greatly changed by the substitution position of the fluorine group.

As described above, the novel condensed polycyclic compound according to aspects of the present invention can exhibit red light emission having a high color purity. In addition, when the position and the number of substituents to be introduced on the condensed polycyclic skeleton, which is a basic skeleton, are changed, fine adjustment of the emission wavelength can be performed in the red spectrum region.

In this embodiment, the calculation was performed in a manner similar to that in Table 1.

TABLE 2

| EXAMPLE COMPOUND NO. | CALCULATED VALUE (S1)/nm | MEASURED VALUE (S1)/nm |
|---|---|---|
| A1 | 568 | 591 |
| A2 | 570 | — |
| A3 | 571 | 593 |
| A4 | 573 | — |
| B1 | 578 | 603 |
| B2 | 580 | — |
| B3 | 583 | — |
| B7 | 580 | 605 |
| C1 | 573 | 593 |
| C4 | 581 | 601 |
| C8 | 579 | 599 |
| D1 | 570 | 587 |
| D3 | 578 | — |
| D5 | 563 | — |
| D7 | 569 | 589 |

As for the substitution positions and the types of substituents, although the above effect can be obtained even if any types of substituents are substituted at any substitution positions, the compounds in the group C may be provided in one case, and a compound represented by the general formula [3] may be provided in once case. The reason for this is that among the condensed polycyclic compounds according to aspects of the present invention, the compounds in the group C having a spiro fluorene skeleton each have the most significant effect of reducing the stack because of its bulky substituent. In addition, it may be the case that substituents are substituted at $R_3$, $R_5$, $R_6$, $R_9$, $R_{11}$, $R_{14}$, and $R_{16}$ since the effect of reducing the stack is further enhanced and such a compound can be easily synthesized. As the type of alkyl group for $R_3$, $R_9$, $R_{11}$, $R_{14}$, and $R_{16}$, a t-butyl group may be provided due to its stereoscopically large bulky property.

[3]

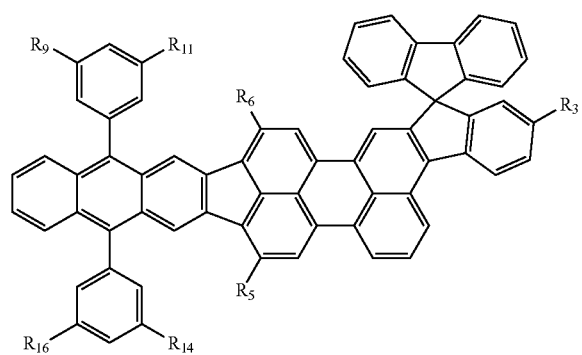

(Description of Synthetic Route)

One example of a synthetic route of the organic compound according to aspects of the present invention will be described. Hereinafter, reaction formulas will be shown.

When the synthesis is performed by using a substituent R selected from the group consisting of a hydrogen atom, a fluorine group, an alkyl group having 1 to 4 carbon atoms, a phenyl group, a biphenyl group, and a terphenyl group, various organic compounds according to aspects of the present invention can be synthesized.
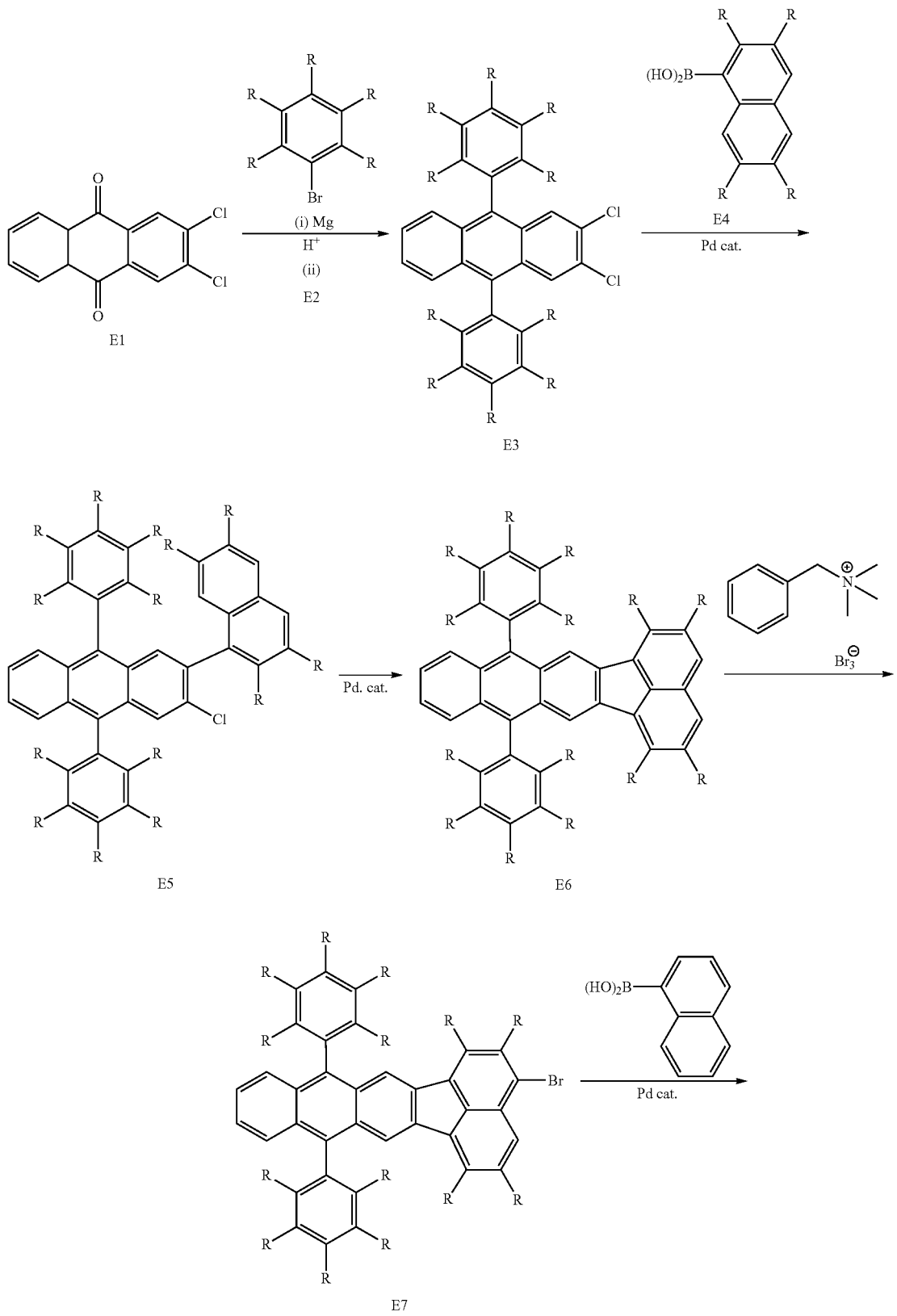

-continued
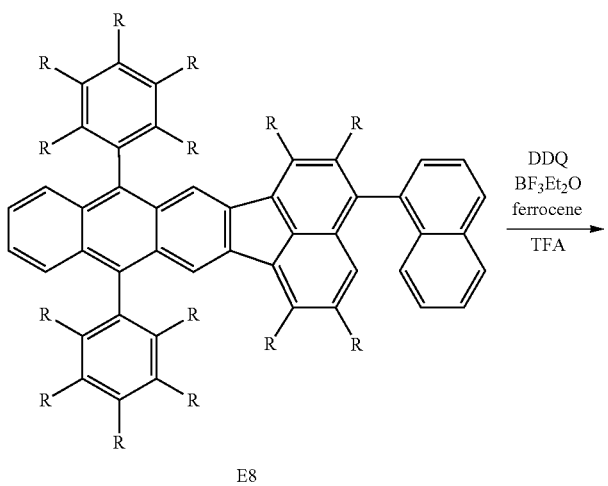
E8
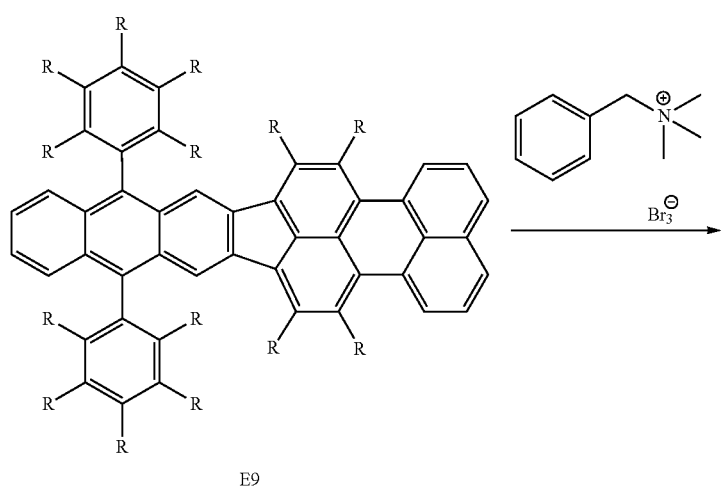
E9
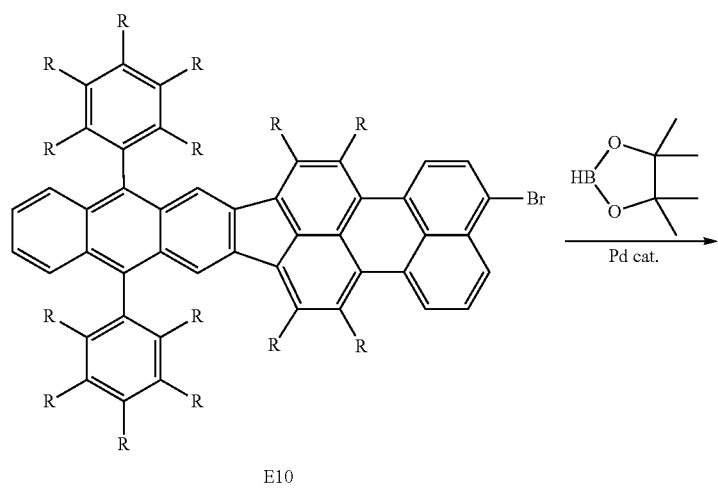
E10

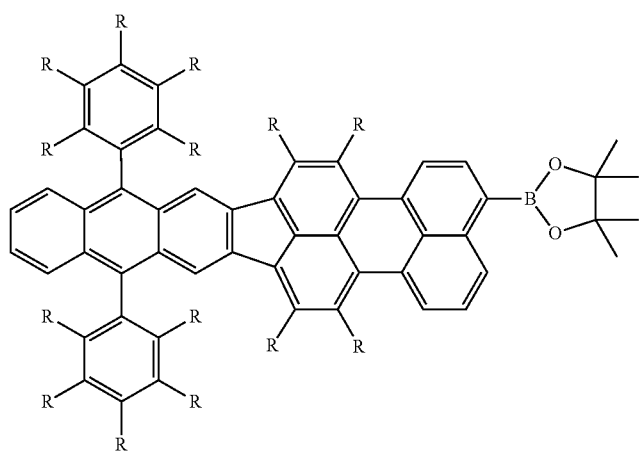
E11
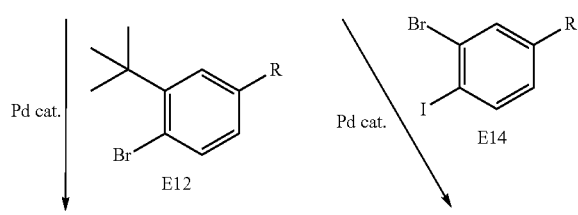
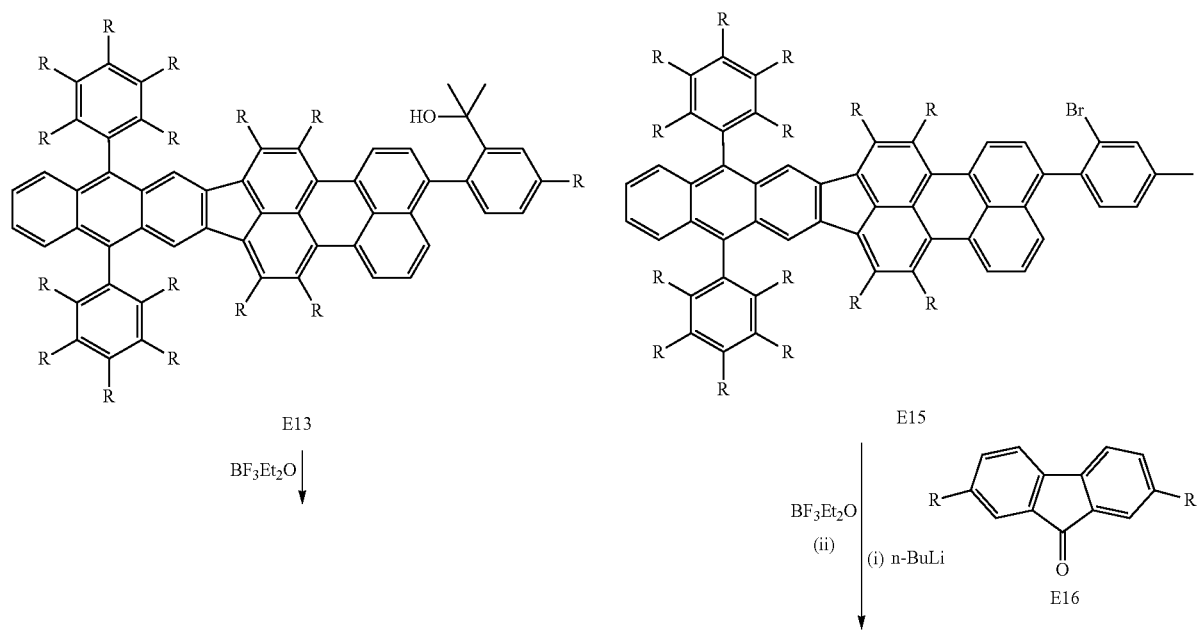

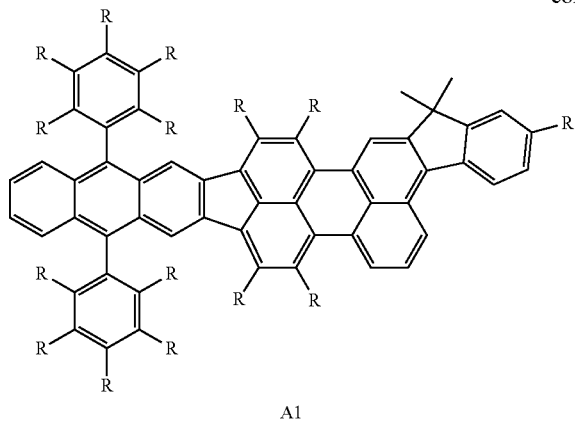

A1

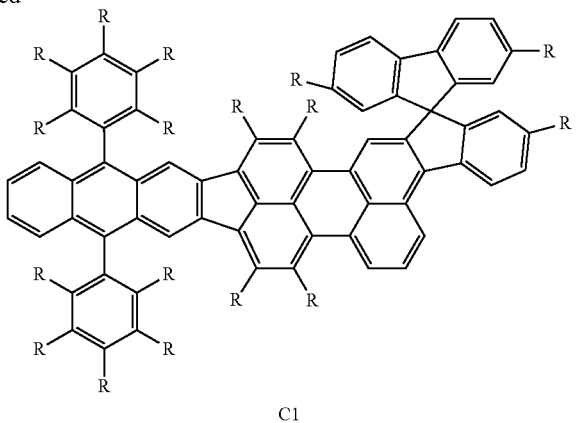

C1

(Description of Organic Light Emitting Element)

Next, an organic light emitting element of this embodiment will be described.

The organic light emitting element of this embodiment includes an anode, a cathode, which are a pair of electrodes, and an organic layer arranged between these two electrodes, and this organic compound layer contains the novel condensed polycyclic compound represented by the general formula [1].

The number of organic compound layers of the organic light emitting element according to aspects of the present invention may be either one or two or more. The plurality of layers are layers each appropriately selected from a hole injection layer, a hole transport layer, a light emitting layer, a hole block layer, an electron transport layer, an electron injection layer, an exciton block layer, and the like. Of course, the plurality of layers may be selected from the above group and may be used in combination. In addition, the light emitting layer may be formed from either a single layer or a plurality of layers. For example, in the case of a white light emitting element, the following light emitting layer structure may be mentioned; however, of course, the structure is not limited thereto.

(1) Single layer: an element containing a blue, a green, and a red light emitting material.

(2) Single layer: an element containing a pale blue and a yellow light emitting material.

(3) Two layers: a multilayer element including a blue light emitting layer and a light emitting layer containing a green and a red light emitting material, or a red light emitting layer and a light emitting layer containing a blue and a green light emitting material.

(4) Two layers: a multilayer element including a pale blue light emitting layer and a yellow light emitting layer.

(5) Three layers: a multilayer element including a blue light emitting layer, a green light emitting layer, and a red light emitting layer.

Figure 3:
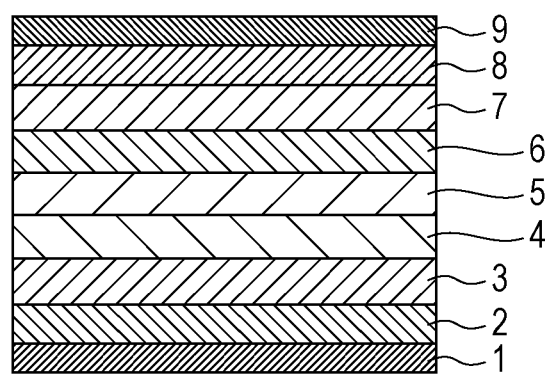
FIG. 3 is a schematic cross-sectional view showing a multilayer organic light emitting element including three light emitting layers, that is, a blue, a green, and a red light emitting layer.

FIG. 3 is a schematic cross-sectional view showing one example of an element structure including three light emitting layers of the above (5) as on example of an organic white light emitting element of this embodiment. In this figure, an organic light emitting element including three light emitting layers which emit the respective colors is shown. The details of the structure will be described below.

This organic light emitting element has an element structure in which an anode 1, a hole injection layer 2, a hole transport layer 3, a blue light emitting layer 4, a green light emitting layer 5, a red light emitting layer 6, an electron transport layer 7, an electron injection layer 8, and a cathode 9 are laminated on a substrate, such as a glass. However, the lamination order of the blue, the green, and the red light emitting layers are not particularly limited.

The white according to aspects of the present invention includes pure white, natural white, and the like. In addition, as the color temperature of the white according to aspects of the present invention, 3,000K to 9,500K may be mentioned. In addition, x and Y of the C.I.E. chromaticity coordinates of the organic white light emitting element according to aspects of the present invention are 0.25 to 0.50 and 0.30 to 0.42, respectively.

The structure of the organic light emitting element of this embodiment is not limited to those described above. Various layer structures can be formed, and for example, an insulating layer may be provided at an interface between the electrode and the organic compound layer, an adhesive layer or an interference layer may be provided, and/or the electron transport layer or the hole transport layer may be formed from two layers having different ionization potentials.

As an element configuration of the above structures, a so-called bottom emission system in which light is extracted from the electrode at a substrate side, a so-called top emission system in which light is extracted from a side opposite to the substrate, and a dual emission system in which light is extracted from both surface sides may be used.

The novel condensed polycyclic compound according to aspects of the present invention may be used as a guest material of the light emitting layer of the organic light emitting element. Furthermore, since emitting light in a red spectrum region, the condensed polycyclic compound according to aspects of the present invention may be used as a guest material of an organic red light emitting element.

The concentration of the guest material to the host material in the light emitting layer of the organic light emitting element of this embodiment may be 0.01 to 30 percent by weight, such as 0.1 to 20 percent by weight.

In addition, the concentration of the host material in the light emitting layer of the organic light emitting element of this embodiment is 50 to 99.9 percent by weight to the total amount of the light emitting layer, such as 80 to 99.5 percent by weight.

In this embodiment, the guest material is a material that actually determines the emission color of the organic light emitting element and is a material that emits light by itself. On the other hand, the host material is a material having a higher composition ratio to the whole light emitting layer than that of the guest material. The host material may be formed of a plurality of materials, and for example, an emission assist material and an electron injection material may also be included.

When the organic compound according to aspects of the present invention is used as the guest material, since the HOMO level is high, and the hole injection property (hole trapping property) is improved, an organic red light emitting element having a high efficiency and a high color purity can be provided.

Furthermore, the novel condensed polycyclic compound according to aspects of the present invention can be effectively used as a red guest material of an organic white light emitting element as described by the above (1), (3), and (5).

Since many red light emitting materials have a small band gap, the LUMO level thereof is low. This can also be applied to the condensed polycyclic compound a-1 disclosed in Japanese Patent Laid-Open No. 2003-272866.

Accordingly, when the red guest material is used for an organic white light emitting element, since electrons are strongly trapped, uniform white light emission is difficult to obtain. That is, since the red guest material strongly emits light, it is difficult for other guest materials having different emission colors to efficiently emit light.

As described above, the novel condensed polycyclic compound according to aspects of the present invention has a high HOMO level, and in addition, the LUMO level thereof is also high (closer to the vacuum level). The results of calculated LUMO levels are shown in Table 3 as those shown in Table 1. It is found that the organic compound according to aspects of the present invention has a higher LUMO level than that of the analogous compound a-2 disclosed in Japanese Patent Laid-Open No. 2003-272866.

Hence, when the novel condensed polycyclic compound according to aspects of the present invention is used as a red guest material of an organic white light emitting element as described by the above (1), (3), and (5), it is expected to obtain white light emission having a high efficiency and a high color purity. The reason for this is that since the LUMO level of the compound according to aspects of the present invention is high, the electron trapping property becomes low, and the other guest materials having different emission colors can efficiently and uniformly emit light.

The novel condensed polycyclic compound according to aspects of the present invention can be used for the hole injection layer of the organic light emitting element. The reason for this is that the organic compound according to aspects of the present invention has a high HOMO level and can assist hole injection from the anode to the organic compound layer.

In this case, the hole injection layer may be formed only from the organic compound according to aspects of the present invention or may be formed therefrom in combination with other materials.

When the organic compound layer according to aspects of the present invention is used for the hole injection layer, since the injection property is improved, an organic light emitting element which can be driven at a low voltage can be provided.

Besides the novel condensed polycyclic compound according to aspects of the present invention, optionally, the organic light emitting element according to aspects of the present invention may also use at least one of currently known low molecular and high molecular hole injection materials, hole transport materials, host materials, guest materials, electron injection materials, electron transport materials, and the like.

Hereinafter, examples of these materials will be described.

As the hole injection material or the hole transport material, a material having a high hole mobility may be provided. As low molecular and high molecular materials each having a hole injection ability or a hole transport ability, for example, there may be mentioned a triarylamine derivative, a phenylenediamine derivative, a stilbene derivative, a phthalocyanine derivative, a porphyrin derivative, a poly(vinyl carbazole), a polythiophene, and other conductive polymers.

As the host material, in particular, the compounds shown in the following Table 4 may be mentioned by way of example.

TABLE 3

| COMPOUND | MOLECULAR STRUCTURAL FORMULA | HOMO (eV) |
|----------|------------------------------|-----------|
| A1       |                              | −2.24     |
| a-2      |                              | −2.48     |

TABLE 4
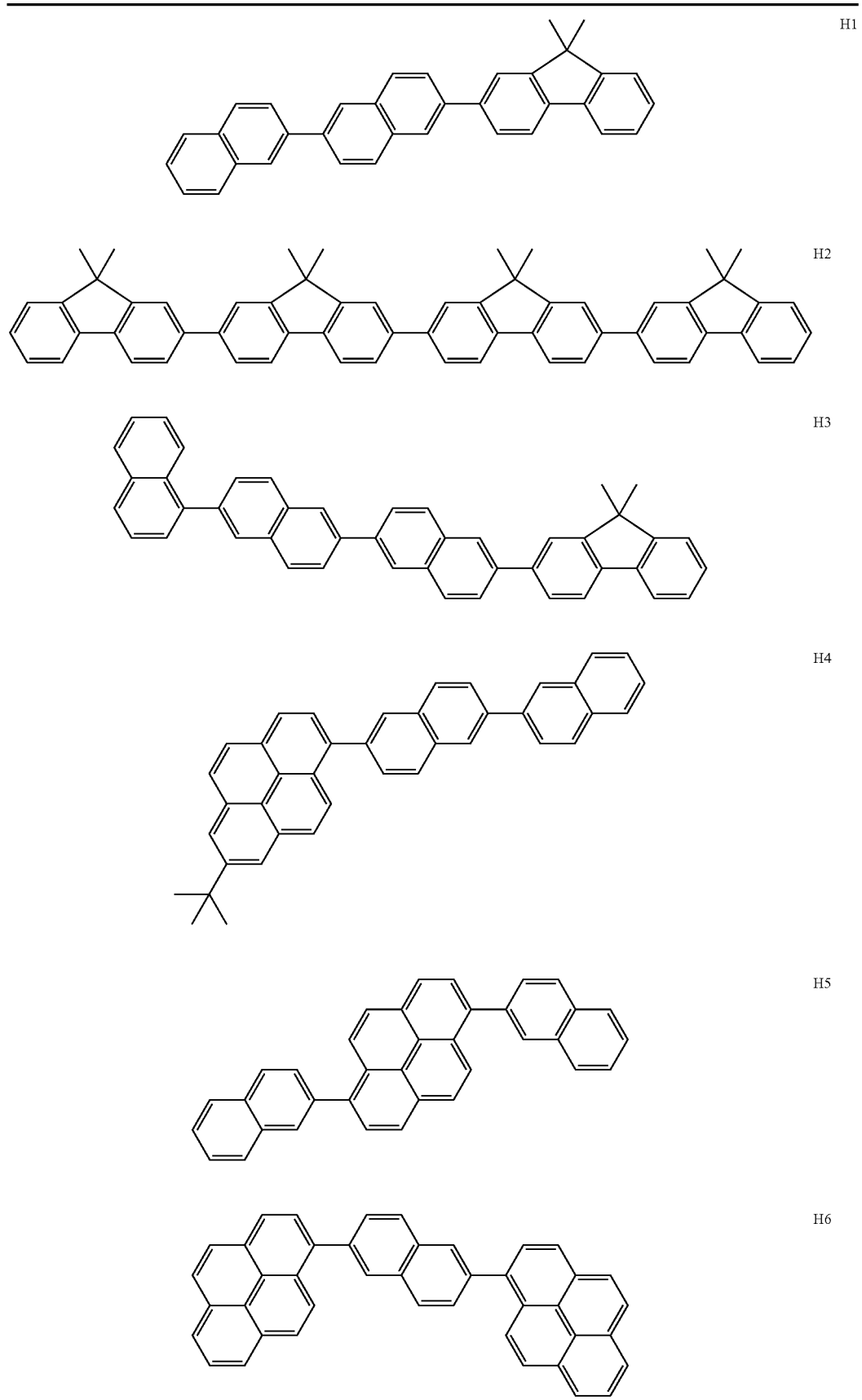

TABLE 4-continued
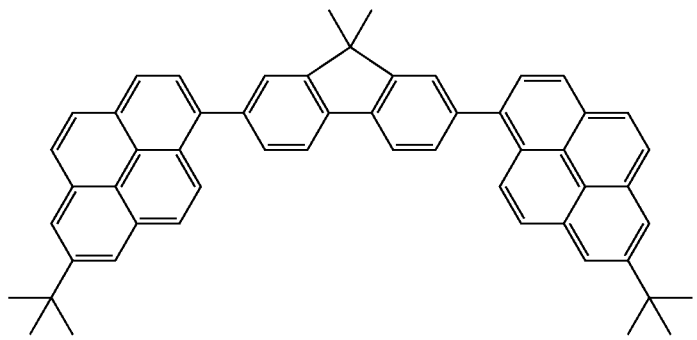 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] H7
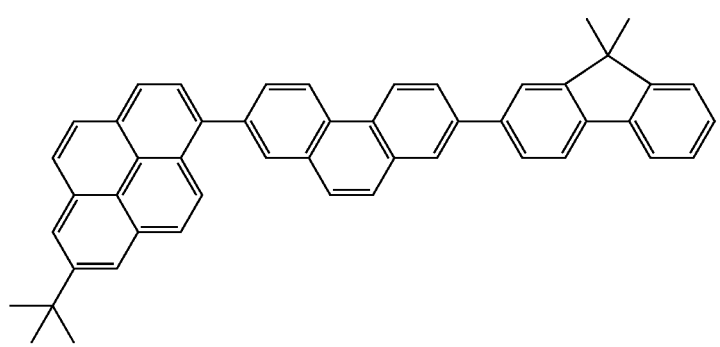 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34] H8
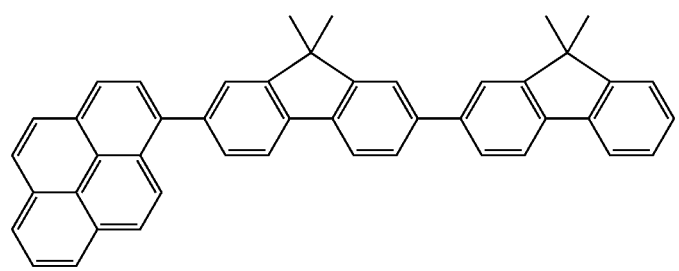 [SMILES: CC1(C)c2ccccc2-c2ccc(-c3ccc4c(c3)C(C)(C)c3cc(-c5ccc6ccc7cccc8ccc5c6c78)ccc3-4)cc21] H9
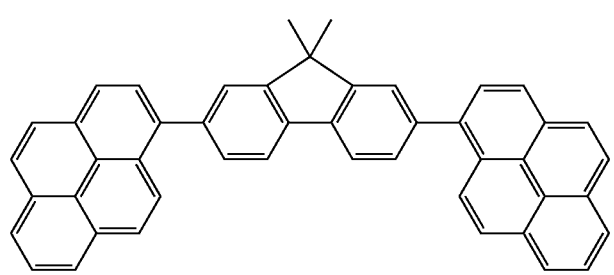 [SMILES: CC1(C)c2cc(-c3ccc4ccc5cccc6ccc3c4c56)ccc2-c2ccc(-c3ccc4ccc5cccc6ccc3c4c56)cc21] H10
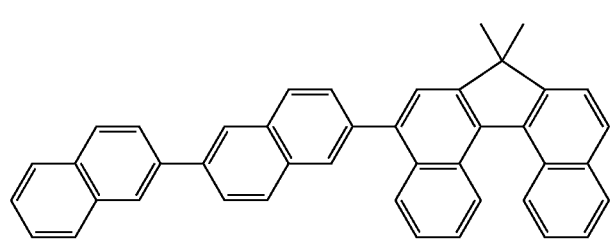 [SMILES: CC1(C)c2ccc3ccccc3c2-c2c1cc(-c1ccc3cc(-c4ccc5ccccc5c4)ccc3c1)c1ccccc21] H11

TABLE 4-continued
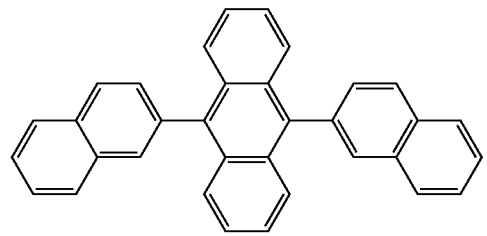 [SMILES: c1ccc2cc(-c3c4ccccc4c(-c4ccc5ccccc5c4)c4ccccc34)ccc2c1] H12
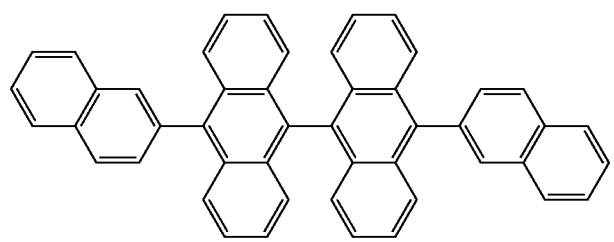 [SMILES: c1ccc2cc(-c3c4ccccc4c(-c4c5ccccc5c(-c5ccc6ccccc6c5)c5ccccc45)c4ccccc34)ccc2c1] H13
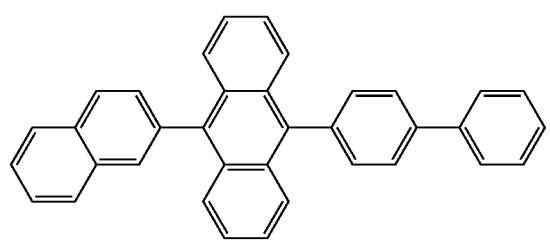 [SMILES: c1ccc(-c2ccc(-c3c4ccccc4c(-c4ccc5ccccc5c4)c4ccccc34)cc2)cc1] H14
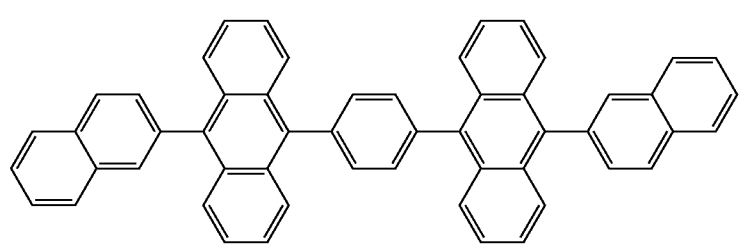 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H15
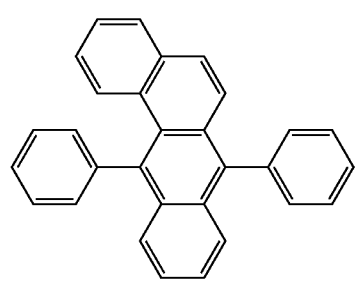 [SMILES: c1ccc(-c2c3ccccc3c(-c3ccccc3)c3c2ccc2ccccc23)cc1] H16

TABLE 4-continued
| | |
|---|---|
| 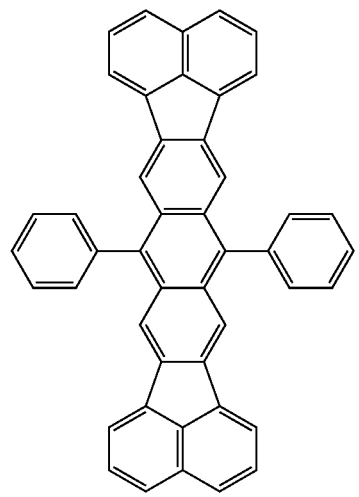 [SMILES: c1ccc(-c2c3cc4c(cc3c(-c3ccccc3)c3cc5c(cc23)-c2cccc3cccc-5c23)-c2cccc3cccc-4c23)cc1] | H17 |
| 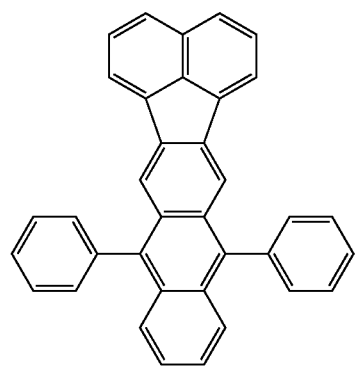 [SMILES: c1ccc(-c2c3ccccc3c(-c3ccccc3)c3cc4c(cc23)-c2cccc3cccc-4c23)cc1] | H18 |
| 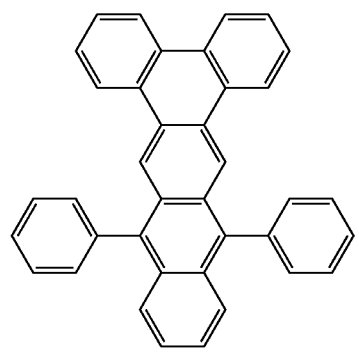 [SMILES: c1ccc(-c2c3ccccc3c(-c3ccccc3)c3cc4c5ccccc5c5ccccc5c4cc23)cc1] | H19 |
| 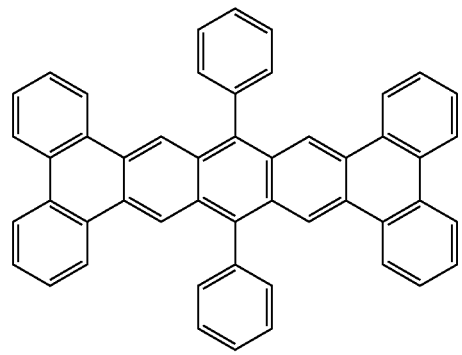 [SMILES: c1ccc(-c2c3cc4c5ccccc5c5ccccc5c4cc3c(-c3ccccc3)c3cc4c5ccccc5c5ccccc5c4cc23)cc1] | H20 |

TABLE 4-continued

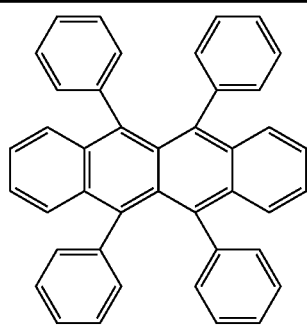

H21

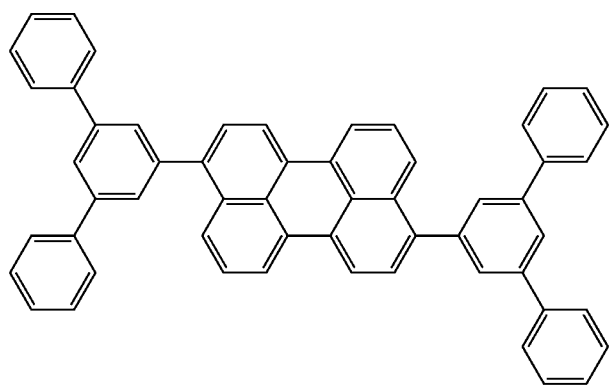 [SMILES: c1ccc(-c2cc(-c3ccccc3)cc(-c3ccc4c5cccc6c(-c7cc(-c8ccccc8)cc(-c8ccccc8)c7)ccc(c7cccc3c74)c65)c2)cc1]

H22

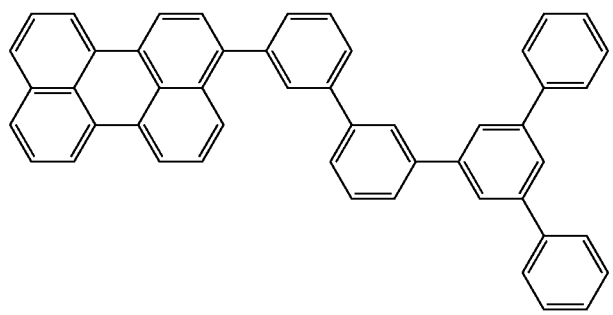 [SMILES: c1ccc(-c2cc(-c3ccccc3)cc(-c3cccc(-c4cccc(-c5ccc6c7cccc8cccc(c9cccc5c96)c87)c4)c3)c2)cc1]

H23

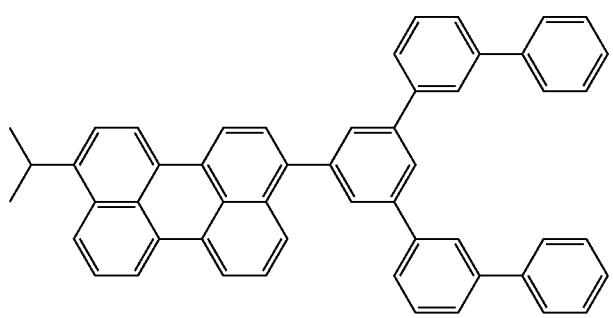 [SMILES: CC(C)c1ccc2c3ccc(-c4cc(-c5cccc(-c6ccccc6)c5)cc(-c5cccc(-c6ccccc6)c5)c4)c4cccc(c5cccc1c52)c43]

H24

However, the present invention is not limited to those shown above. Derivatives of the compounds shown in Table 2 may also be used as the host material. In addition, besides those mentioned above, for example, there may also be mentioned a condensed ring compound (such as a fluorene derivative, a naphthalene derivative, an anthracene derivative, a pyrene derivative, a carbazole derivative, a quinoxaline derivative, or a quinoline derivative), an organic aluminum complex such as tris(8-quinolate)aluminum, an organic zinc complex, a triphenylamine derivative, and a polymer derivative, such as a polyfluorene derivative, or a polyphenylene derivative. However, of course, the host material is not limited to those mentioned above.

In the organic white light emitting element, a fluorescent light emitting dopant other than the organic compound according to aspects of the present invention may also be used together, and for example, there may be mentioned a condensed ring compound (such as a fluorene derivative, a naphthalene derivative, a pyrene derivative, a perylene derivative, a tetracene derivative, an anthracene derivative, or rubrene), a quinacridone derivative, a coumarin derivative, a stilbene derivative, an organic aluminum complex such as tris(8-quinolate)aluminum, an organic beryllium complex, and a polymer derivative, such as a poly(phenylene vinylene) derivative, a polyfluorene derivative, or a polyphenylene derivative. However, of course, the fluorescent light emitting dopant is not limited to those mentioned above.

The electron injection material or the electron transport material is selected, for example, in consideration of the balance with the hole mobility of the hole injection material or the hole transport material. As a material having an electron injection ability or an electron transport material, for example, there may be mentioned an oxadiazole derivative, an oxazole derivative, a pyrazine derivative, a triazole derivative, a triazine derivative, a quinoline derivative, a quinoxaline derivative, a phenanthroline derivative, and an organic aluminum complex. However, of course, the electron injection or transport material is not limited to those mentioned above.

A material having a higher work function may be used as an anode material. For example, a metal itself, such as gold, platinum, silver, copper, nickel, palladium, cobalt, selenium, vanadium, or tungsten, an alloy thereof, and a metal oxide, such as tin oxide, zinc oxide, indium oxide, indium tin oxide (ITO), or indium zinc oxide, may be used. In addition, conductive polymers, such as a polyaniline, a polypyrrole, and a polythiophene, may also be used. These electrode materials may be used alone, or at least two types thereof may also be used in combination. In addition, the anode may be formed from either one layer or a plurality of layers.

On the other hand, a material having a low work function may be used as a cathode material. For example, an alkali metal, such as lithium or cesium, an alkaline earth metal, such as calcium, and a metal itself, such as aluminum, titanium, manganese, silver, lead, or chromium, may be mentioned. Alternatively, an alloy formed in combination of the above metals may also be used. For example, magnesium-silver, aluminum-lithium, and aluminum-magnesium may be used. A metal oxide, such as indium tin oxide (ITO), may also be used. These electrode materials may be used alone, or at least two types thereof may also be used in combination. In addition, the cathode may be formed from either one layer or a plurality of layers.

The layers of the organic light emitting element of this embodiment are each formed by the following method.

In general, the layer is formed by a vacuum deposition method, an ionized deposition method, a sputtering method, a plasma method, or a known coating method (such as a spin coating method, a dipping method, a casting method, an LB method, or an ink jet method) in which the organic compound is dissolved in an appropriate solvent. When the layer is formed by a vacuum deposition method, a solution coating method, or the like, for example, crystallization is not likely to occur, and an excellent aging stability can be obtained. In addition, when film formation is performed by a coating method, a film may also be formed in combination with an appropriate binder resin.

As the above binder resin, although a poly(vinyl carbazole) resin, a polycarbonate resin, a polyester resin, an ABS resin, an acrylic resin, a polyimide resin, a phenol resin, an epoxy resin, a silicone resin, and an urea resin may be mentioned by way of example, the binder resin is not limited thereto. In addition, these binder resins may be used alone as a homopolymer or a copolymer, or at least two types thereof may be used in combination. Furthermore, optionally, additives, such as a known plasticizer, antioxidant, and ultraviolet absorber, may also be used together.

As the substrate of the organic light emitting element, although an insulating member such as a glass may be used, a semiconductor such as silicon may also be used.

(Application of Organic Light Emitting Element)

The organic light emitting element according to aspects of the present invention may be used for a display device and a lighting device. In addition, the organic light emitting element according to aspects of the present invention may also be used, for example, for an exposure light source of an image forming device of an electrophotographic system and a backlight of a liquid crystal display device.

In the case in which the organic light emitting element according to aspects of the present invention is a white light emitting element, when being used in combination with a color filter, the above organic light emitting element can be used for a display device and a lighting device.

The display device has the organic light emitting element of this embodiment in a display portion. This display portion has a plurality of pixels. This pixel has the organic light emitting element of this embodiment and a TFT element, which is one example of a switching element, to control the emission luminance, and a drain electrode or a source electrode of the TFT element is connected to the anode or the cathode of this organic light emitting element. The display device may be used as an image display device of a personal computer (PC) or the like. The TFT element is provided on an insulating surface of the substrate.

The display device may be an image input device which has an image input portion to input image information from an area CCD, a linear CCD, a memory card, or the like, and which outputs an input image on the display portion. In addition, as a display portion of an image forming device or an ink jet printer, the display device may have both an image output function to display image information input from the outside and an input function as an operation panel to input processing information for the image. In addition, the display device may also be used for a display portion of a multifunctional printer.

Figure 4:
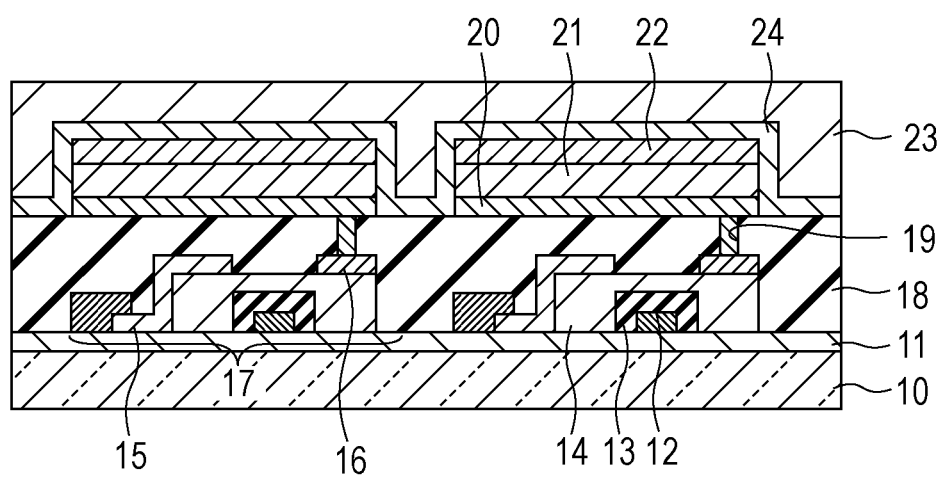
FIG. 4 is a schematic cross-sectional view showing an organic light emitting element and a switching element connected thereto.

FIG. 4 is a schematic cross-sectional view of a display device having the organic light emitting element of this embodiment and a TFT element, which is one example of a switching element, connected to the above organic light emitting element. In this figure, two sets each containing the organic light emitting element and the TFT element are shown. The details of the structure will be described.

This display device includes a substrate 10 formed of a glass or the like and a dampproof film 11 provided thereon to protect the TFT element or the organic compound layer. In addition, reference numeral 12 indicates a metal gate electrode. Reference numeral 13 indicates a gate insulating film, and reference numeral 14 indicates a semiconductor layer.

A TFT element 17 includes the semiconductor layer 14, a drain electrode 15, and a source electrode 16. An insulating film 18 is provided on an upper portion of the TFT element 17. An anode 20 of the organic light emitting element and the source electrode 16 are connected to each other through a contact hole 19. The structure of the display device is not limited to that described above, and any structure may be used as long as the anode or the cathode is connected to one of the source electrode and the drain electrode of the TFT element.

In this figure, many organic compound layers are collectively shown as one single organic compound layer 21. On a cathode 22, a first protective layer 23 and a second protective layer 24 are provided to suppress degradation of the organic light emitting element.

In the display device of this embodiment, the switching element is not particularly limited. For example, an MIM element or an a-Si transistor element may also be used. The switching element may also be provided on a semiconductive surface. The semiconductive surface is for example, a surface of a silicon substrate.

In addition, when the organic light emitting element according to aspects of the present invention is used as a lighting device, without providing the switching element as described above, the structure may be formed in such a way that conductive wires to be conducted to a power source and a switching unit are connected to the respective electrodes. Furthermore, in this case, an inverter converting an alternating voltage to a direct current voltage may be provided for the lighting device.

In addition, by using the white light emitting element described above, a lighting device which emits white light can be formed.

EXAMPLES

Example 1

Synthesis of Example Compound (C1)

After a toluene solvent (42 ml) was deaerated, 0.28 g (1.25 mmol) of palladium acetate(II) and 0.62 g (2.50 mmol) of s-phos were added and were then stirred for 10 minutes at room temperature. Subsequently, after 4.74 g (12.5 mmol) of the compound (F2), 3.19 g (2.50 mmol) of potassium phosphate, and distilled water (1 ml) were added, 5.0 g (12.5 mmol) of the compound (F1) was finally added, and stirring was performed at 95° C. for 3 hours. After cooling, methanol was added, and filtration was then performed. After chlorobenzene (500 ml) was added to this residue and was heated to 100° C., this solution in this state was then processed by a silica gel column chromatography (moving phase; toluene) followed by condensation. After the condensed product was dispersed and washed with acetone, filtration was performed followed by drying, so that 5.96 g of the orange solid (F3) was obtained (yield: 77%).

After a DMF solvent (180 ml) was deaerated, 4.09 g (4.47 mmol) of $Pd_2(dba)_3(0)$ and 2.51 g (8.94 mmol) of tricyclohexylphosphine were added and were then stirred for 15 minutes at room temperature. Subsequently, after 5.50 g (8.94 mmol) of the compound (F3) and 5.44 g (35.8 mmol) of DBU were added, stirring was performed at 140° C. for 3.5 hours. After cooling, methanol (200 ml) was added, and filtration was then performed. After toluene (500 ml) was added to this residue and was heated to 100° C., this solution in this state was then processed by a silica gel column chromatography (moving phase; toluene) followed by condensation. After the condensed product was dispersed and washed with acetone, filtration was performed followed by drying, so that 4.52 g of the reddish orange solid (F4) was obtained (yield: 87%).

After a dichloromethane solvent (140 ml) was deaerated, 4.00 g (6.91 mmol) of the compound (F4) was dissolved therein. To this solution, 2.70 g (6.91 mmol) of benzyltrimethylammonium tribromide was added and was then stirred for 5 hours at room temperature. Subsequently, methanol (150 ml) was added to the above solution and was then filtrated. After chlorobenzene (300 ml) was added to this residue and was heated to 100° C., this solution in this state was then processed by a silica gel column chromatography (moving phase; toluene) followed by condensation. After the condensed product was dispersed and washed with acetone, filtration was performed followed by drying, so that 4.14 g of the reddish brown solid (F5) was obtained (yield: 91%).

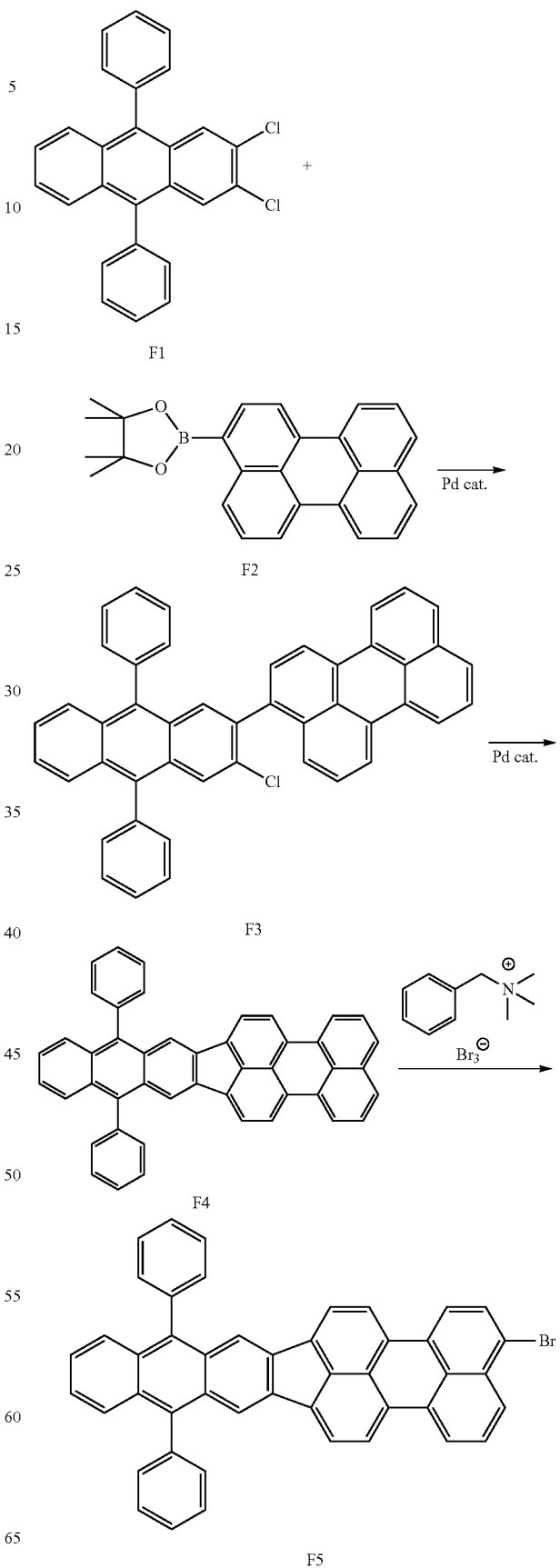

After a 1,4-dioxane solvent (25 ml) was deaerated, 1.50 g (2.28 mmol) of the compound (F5), 1.16 g (4.56 mmol) of the compound (F6), 93 mg (0.114 mmol) of PdCl$_2$(dppf).CH$_2$Cl$_2$ (II), and 448 mg (4.56 mmol) of potassium acetate were added, and stirring was then performed at 80° C. for 3 hours. After cooling, methanol was added, and filtration was then performed. This residue was then processed by a silica gel column chromatography (moving phase; heptane:toluene=1:1) followed by condensation. After the condensed product was dispersed and washed with methanol, filtration was performed followed by drying, so that 921 mg of the red solid (F7) was obtained (yield: 57%).

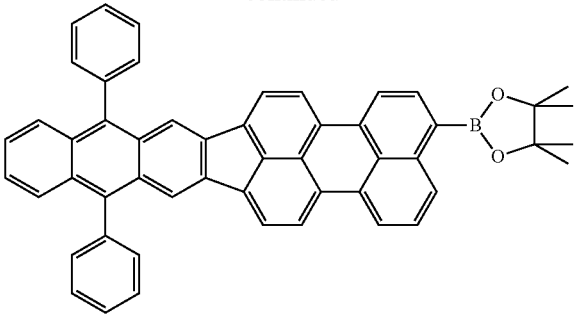

F7

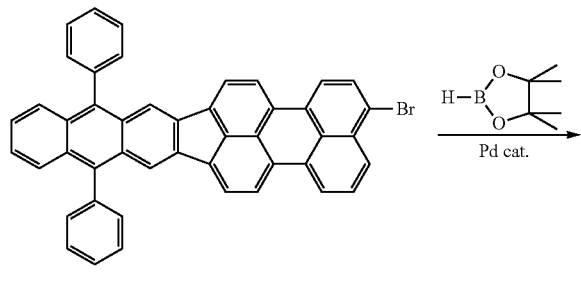

F5

After a mixed solvent of toluene (10 ml) and 1,4-dioxane (4 ml) was deaerated, 500 mg (0.71 mmol) of the compound (F7), 800 mg (2.8 mmol) of the compound (F8), 49 mg (0.043 mmol) of Pd(PPh$_3$)$_4$(0), and 460 mg (1.4 mmol) of cesium carbonate were added, and stirring was then performed at 100° C. for 12 hours. After cooling, methanol was added, and filtration was then performed. This residue was then processed by a silica gel column chromatography (moving phase; heptane:toluene=3:1) followed by condensation. After the condensed product was dispersed and washed with methanol, filtration was performed followed by drying, so that 430 mg of the red solid (F9) was obtained (yield: 83%).

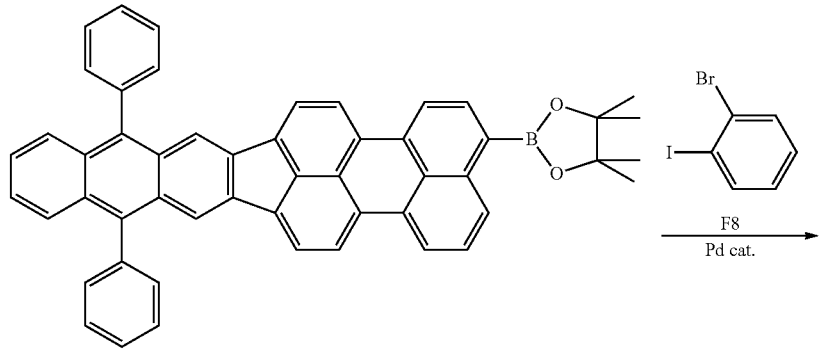

F7

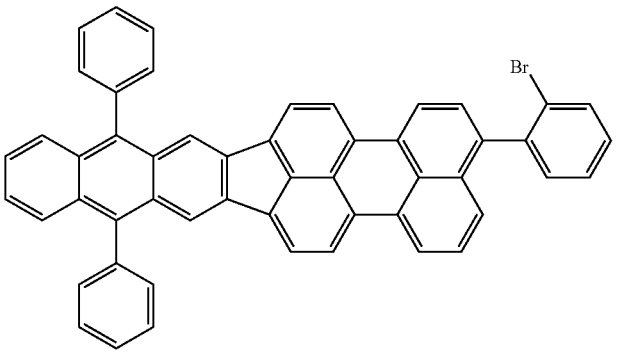

F9

In tetrahydrofuran (2.5 ml), 100 mg (0.14 mmol) of the compound (F9) was dissolved and was then cooled to −78° C. To this solution, 0.09 ml (0.15 mmol) of n-butyl lithium was dripped, and while the temperature was gradually increased to room temperature, stirring was performed for 2 hours. After this solution was again cooled to −78° C., 37 mg (0.20 mmol) of the compound (F10) dissolved in tetrahydrofuran (0.5 ml) was dripped. While the temperature of this solution was gradually increased to room temperature, stirring was performed for 2 hours. After a saturated ammonium chloride aqueous solution (10 ml) was added, extraction was performed with dichloromethane, and condensation was then performed. After dichloromethane (40 ml) was added to the residue thus obtained, boron trifluoro diethyl etherate (0.1 ml) was dripped thereto, and stirring was then performed for 1 hour at room temperature. To this solution, methanol was added, and filtration was then performed. This residue was processed by a silica gel column chromatography (moving phase:heptane:chloroform=3:1) followed by condensation. After this condensed product was dispersed and washed with methanol, filtration was performed followed by drying, so that 30 mg of the red brown solid (F11) (example compound (C1)) was obtained (yield: 27%).

By a mass spectrometry, M+ of the compound (F11) (example compound (C1)) was confirmed to be 817.

When the emission spectrum of the example compound (C1) in a toluene diluted solution was measured at room temperature, the maximum emission wavelength was 593 nm. As the measurement apparatus, a spectral photometer U-3010 manufactured by Hitachi Ltd. was used.

Example 2

Synthesis of Example Compound (A1)

The following synthetic reaction was performed as in the case of Example 1 except that the compound (F8) was changed to the following compound (F12), so that the following compound (F14) (example compound (A1)) was synthesized.

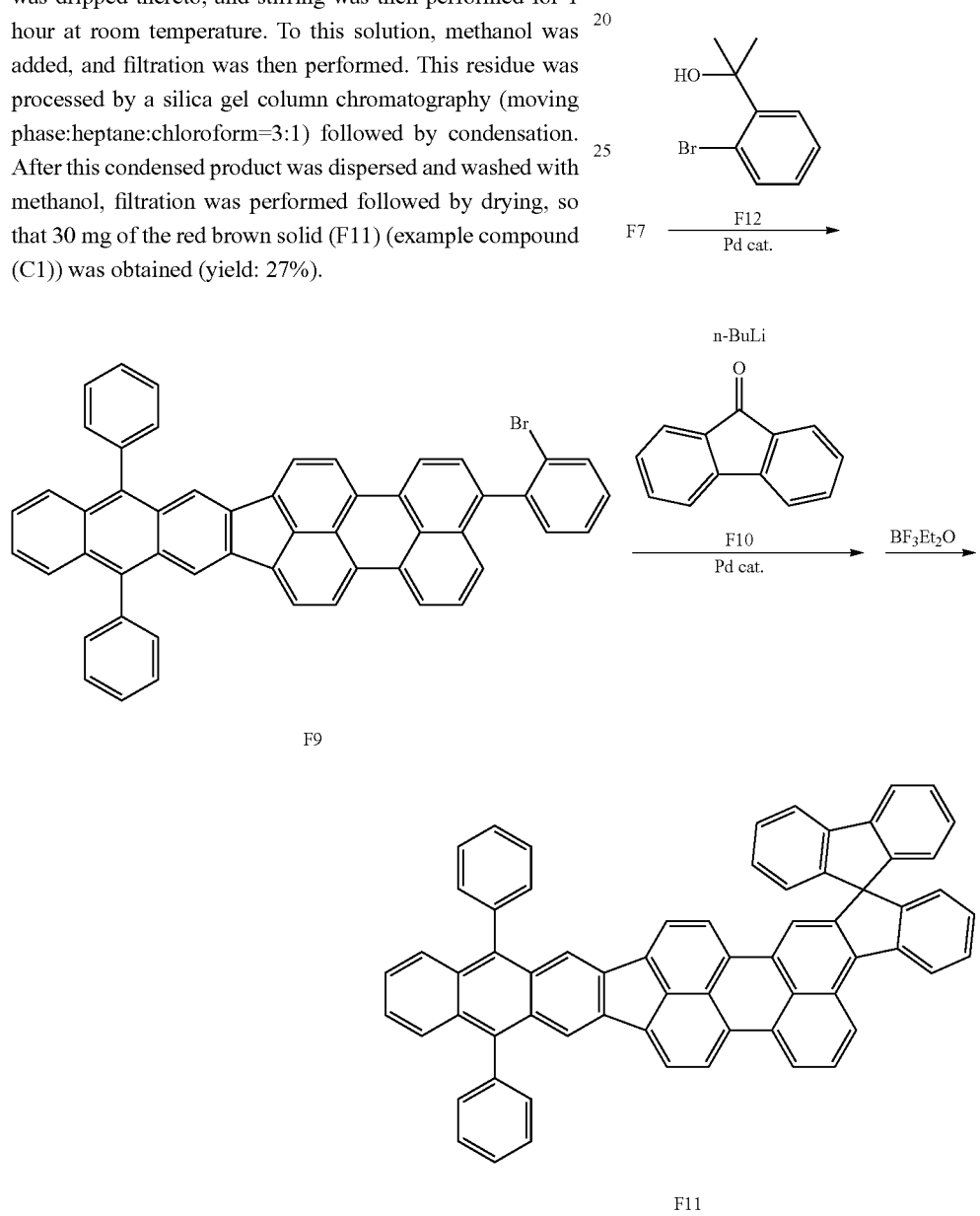

-continued

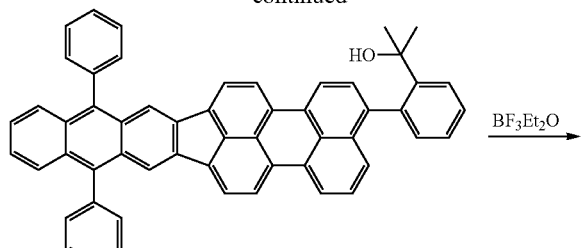

F13

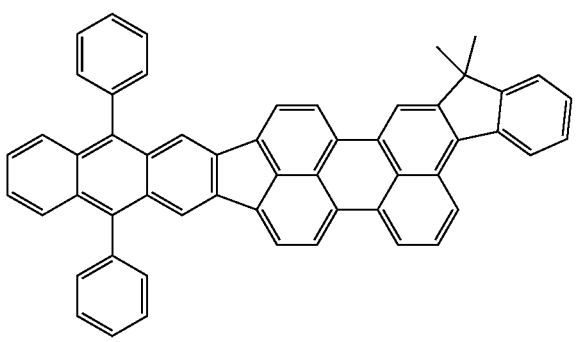

F14

After a toluene solvent (18 ml) was deaerated, 39 mg (0.043 mmol) of Pd$_2$(dba)$_3$(0) and 61 mg (0.13 mmol) of x-phos were added and were then stirred for 10 minutes at room temperature. Subsequently, after 600 mg (0.85 mmol) of the compound (F7), 192 mg (0.89 mmol) of the compound (F12), 540 mg (2.6 mmol) of potassium phosphate, and distilled water (0.5 ml) were added, stirring was performed at 120° C. for 2 hours. After cooling, extraction was performed with toluene, and drying was then performed with sodium sulfate. After condensation was performed, the product thus obtained was then processed by a silica gel column chromatography (moving phase; toluene), and condensation and drying were then performed.

After chloroform (50 ml) was added to this residue to form a solution thereof, boron trifluoro diethyl etherate (0.15 ml) was dripped thereto at 0° C., and stirring was then performed for 12 hour at room temperature. To this solution, methanol was added, and filtration was then performed. This residue was dispersed and washed with a mixed solvent of heptane and toluene, and filtration was then performed followed by drying, so that 389 mg of the red brown solid (F14) (example compound (A1)) was obtained (yield: 66%).

By a mass spectrometry, M+ of the compound (F14) (example compound (A1)) was confirmed to be 694.

In addition, as in the case of Example 1, when the emission spectrum of the example compound (A1) in a toluene diluted solution was measured at room temperature, the maximum emission wavelength was 591 nm.

Example 3

Synthesis of Example Compound (B1)

Except that the compound (F12) was changed to the following compound (F15), the example compound (B1) was synthesized in a manner similar to that of Examples 1 and 2.

By a mass spectrometry, M+ of the example compound (B1) was confirmed to be 770.

In addition, as in the case of Example 1, when the emission spectrum of the example compound (B1) in a toluene diluted solution was measured at room temperature, the maximum emission wavelength was 603 nm.

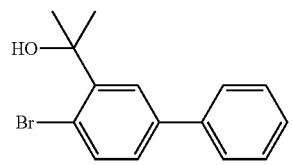

F15

Example 4

Synthesis of Example Compound (A5)

Except that the compound (F1) was changed to the following compound (F16), and the compound (F2) was changed to the following compound (F17), the following compound (F18) was synthesized instead of the compound (F5) in a manner similar to that of Example 1. Subsequently, the following compound (F22) was synthesized as shown below using the compound (F18) as a starting material.

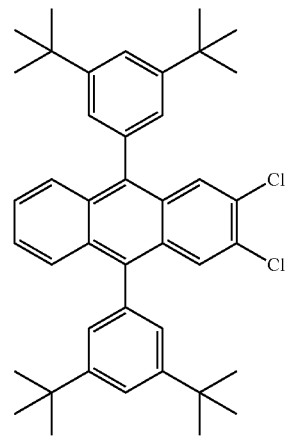

F16

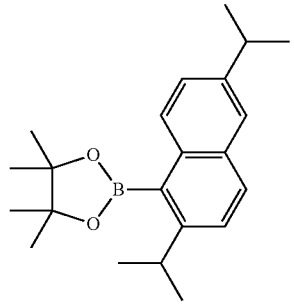

F17

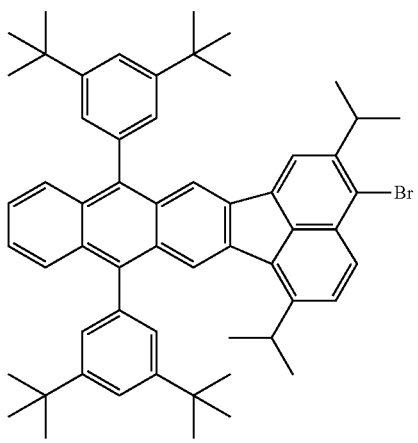

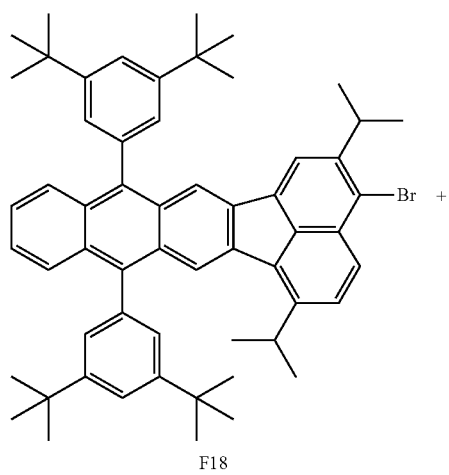

F18

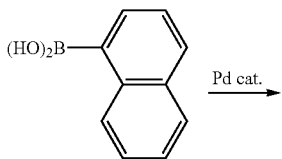

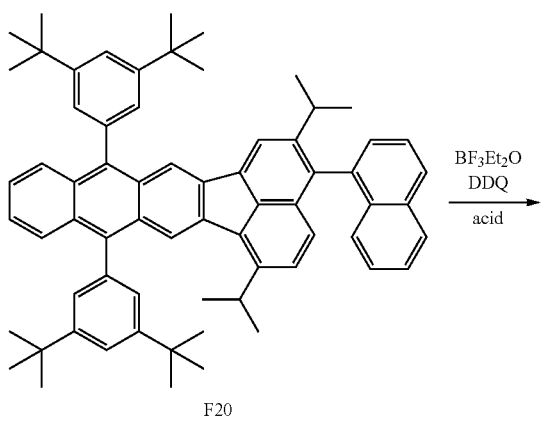

F20

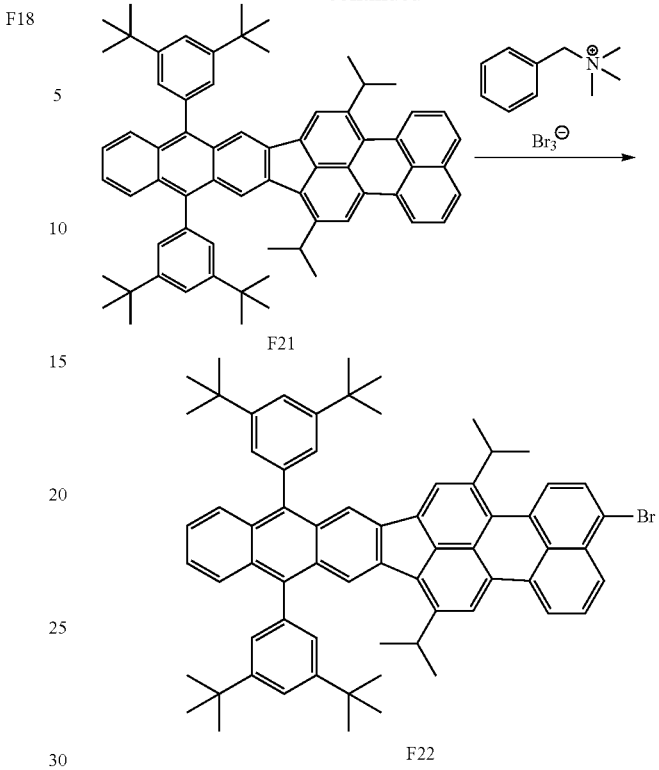

After a toluene solvent (20 ml) was deaerated, 1.0 g (1.18 mmol) of the compound (F18), 245 mg (1.43 mmol) of the compound (F19), 16 mg (0.07 mmol) of Pd(OAc)$_2$(II), 49 mg (0.12 mmol) of s-phos, and 501 mg (2.36 mmol) of potassium phosphate were added, and water (0.5 ml) was also finally added. The solution thus prepared was then stirred at 90° C. for 4 hours. After cooling, extraction was performed with toluene, and drying was then performed with sodium sulfate. After condensation was performed, a residue was purified by a silica gel column chromatography (moving phase; heptane: chloroform=5:1), and condensation was then performed. After the condensed product was dispersed and washed with methanol, filtration was performed followed by drying, so that 735 mg of the yellow solid F20 was obtained (yield: 70%).

To a suspension containing 700 mg (0.79 mmol) of F20 and trifluoro acetic acid (40 ml), 2.5 ml (20 mmol) of boron trifluoro diethyl etherate and 540 mg (2.4 mmol) of DDQ were added, and stirring was then performed for 30 minutes at room temperature. Subsequently, after 450 mg (2.4 mmol) of ferrocene was added, stirring was further performed for 1 hour. Methanol (50 ml) was added thereto, and filtration was then performed. The residue thus obtained was purified by silica gel column chromatography (moving phase: toluene), and condensation was then performed. After this condensed product was dispersed and washed with methanol, filtration was performed followed by drying, so that 477 mg of the orange solid F21 was obtained (yield: 68%).

After a dichloromethane solvent (5 ml) was deaerated, 450 mg (0.51 mmol) of the compound (F21) was dissolved therein. To this solution, 199 mg (0.51 mmol) of benzyltrimethylammonium tribromide was added and was then stirred for 5 hours at room temperature. After methanol (20 ml) was added to this solution, and filtration was then performed, washing was performed with methanol. Next, drying was performed, so that 439 mg of the red solid (F22) was obtained (yield: 89%).

Subsequently, except that the compound (F12) was changed to the following compound (F23), the example compound (A5) was synthesized in a manner similar to that of Example 2.

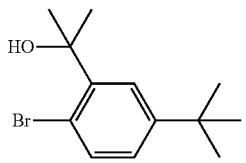

F23

By a mass spectrometry, M+ of the example compound (A5) was confirmed to be 1,059.

In addition, as in the case of Example 1, when the emission spectrum of the example compound (A5) in a toluene diluted solution was measured at room temperature, the maximum emission wavelength was 593 nm.

Example 5

Synthesis of Example Compound (A6)

Except that the compound (F16) was changed to the following compound (F24), and the compound (F17) was changed to the following compound (F25), the example compound (A6) was synthesized in a manner similar to that of Example 4.

By a mass spectrometry, M+ of the example compound (A6) was confirmed to be 863.

In addition, as in the case of Example 1, when the emission spectrum of the example compound (A6) in a toluene diluted solution was measured at room temperature, the maximum emission wavelength was 597 nm.

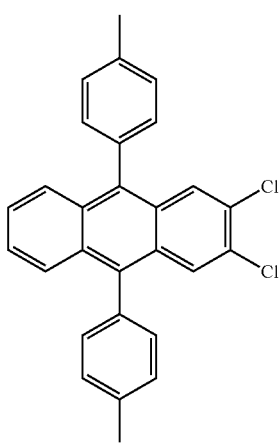

F24

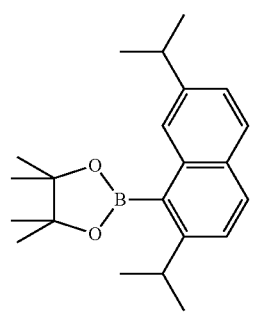

F25

Example 6

Synthesis of Example Compound (A7)

Except that the compound (F16) was changed to the following compound (F26), the compound (F17) was changed to the following compound (F25), and the compound (F23) was changed to the following compound (F27), the example compound (A7) was synthesized in a manner similar to that of Example 4.

By a mass spectrometry, M+ of the example compound (A7) was confirmed to be 905.

In addition, as in the case of Example 1, when the emission spectrum of the example compound (A7) in a toluene diluted solution was measured at room temperature, the maximum emission wavelength was 597 nm.

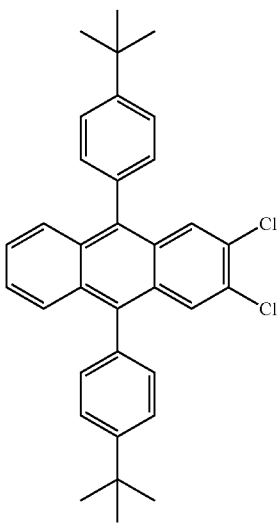

F26

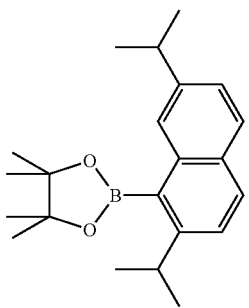

F27

Example 7

Synthesis of Example Compound (B4)

Except that the compound (F17) was changed to the following compound (F28), and the compound (F23) was changed to the following compound (F29), the example compound (B4) was synthesized in a manner similar to that of Example 4.

By a mass spectrometry, M+ of the example compound (B4) was confirmed to be 923.

In addition, as in the case of Example 1, when the emission spectrum of the example compound (B4) in a toluene diluted solution was measured at room temperature, the maximum emission wavelength was 606 nm.

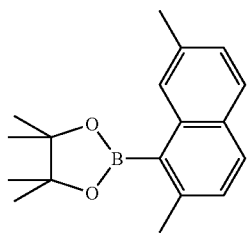

F28

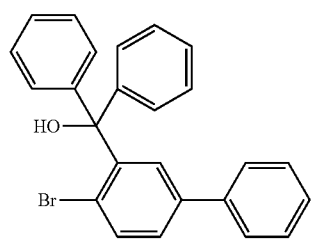

F29

Example 8

Synthesis of Example Compound (B7)

Except that the compound (F17) was changed to the following compound (F30), and the compound (F23) was changed to the following compound (F31), the example compound (B7) was synthesized in a manner similar to that of Example 4.

By a mass spectrometry, M+ of the example compound (B7) was confirmed to be 1,043.

In addition, as in the case of Example 1, when the emission spectrum of the example compound (B7) in a toluene diluted solution was measured at room temperature, the maximum emission wavelength was 605 nm.

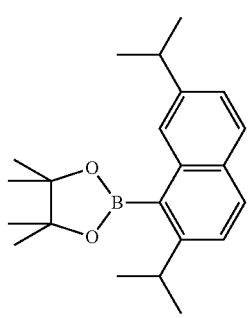

F30

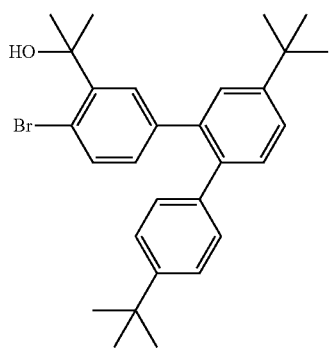

F31

Example 9

Synthesis of Example Compound (C4)

Except that the compound (F23) was changed to the following compound (F32), the example compound (C4) was synthesized in a manner similar to that of Examples 1 and 4.

By a mass spectrometry, M+ of the example compound (C4) was confirmed to be 1,097.

In addition, as in the case of Example 1, when the emission spectrum of the example compound (C4) in a toluene diluted solution was measured at room temperature, the maximum emission wavelength was 601 nm.

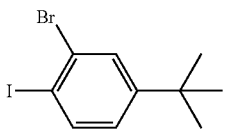

F32

Example 10

Synthesis of Example Compound (C8)

Except that the compound (F10) was changed to the following compound (F33), the example compound (C8) was synthesized in a manner similar to that of Examples 1 and 4.

By a mass spectrometry, M+ of the example compound (C8) was confirmed to be 1,153.

In addition, as in the case of Example 1, when the emission spectrum of the example compound (C8) in a toluene diluted solution was measured at room temperature, the maximum emission wavelength was 599 nm.

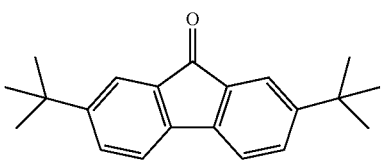

F33

Example 11

Synthesis of Example Compound (D1)

Except that the compound (F12) was changed to the following compound (F34), the example compound (D1) was synthesized in a manner similar to that of Example 2.

By a mass spectrometry, M+ of the example compound (D1) was confirmed to be 712.

In addition, as in the case of Example 1, when the emission spectrum of the example compound (D1) in a toluene diluted solution was measured at room temperature, the maximum emission wavelength was 587 nm.

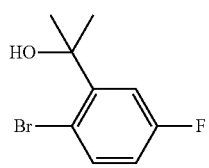

F34

Example 12

Synthesis of Example Compound (D7)

Except that the compound (F1) was changed to the following compound (F35), the example compound (D7) was synthesized in a manner similar to that of Example 1.

By a mass spectrometry, M+ of the example compound (D7) was confirmed to be 852.

In addition, as in the case of Example 1, when the emission spectrum of the example compound (D7) in a toluene diluted solution was measured at room temperature, the maximum emission wavelength was 589 nm.

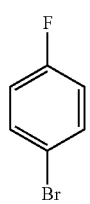

F35

Example 13

In this example, an organic light emitting element having the structure in which an anode/hole injection layer/hole transport layer/light emitting layer/electron transport layer/electron injection layer/cathode were sequentially provided on a substrate was formed by the following method.

An ITO film having a thickness of 120 nm formed as an anode on a glass substrate by a sputtering method was used as a transparent conductive support substrate (ITO substrate). The following organic compound layers and electrode layers were successively formed on this ITO substrate using vacuum deposition performed by resistance heating in a vacuum chamber at a pressure of $10^{-5}$ Pa. In this case, the electrode surfaces facing each other were each formed to have an area of 3 mm$^2$.

Hole injection layer (30 nm) Compound (G1)

Hole transport layer (10 nm) Compound (G2)

Light emitting layer (30 nm) Host: Compound (G3) (Weight ratio: 99.5%), Guest: Compound (C1) (Weight ratio: 0.5%)

Electron transport layer (30 nm) Compound (G4)

Electron injection layer (1 nm) LiF

Metal electrode layer (100 nm) Al

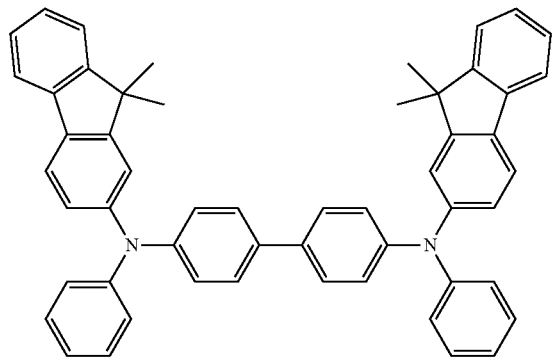

G1

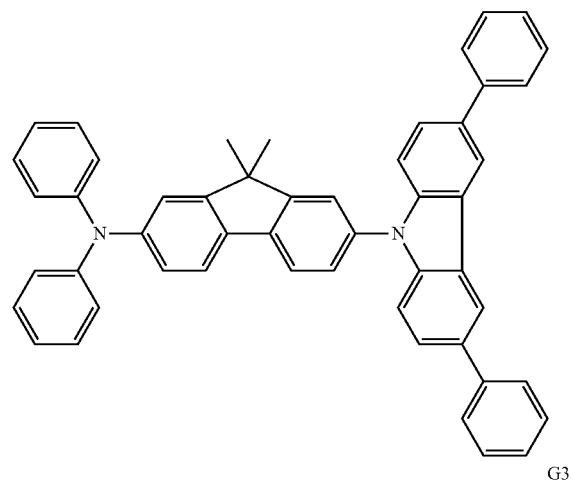

G2

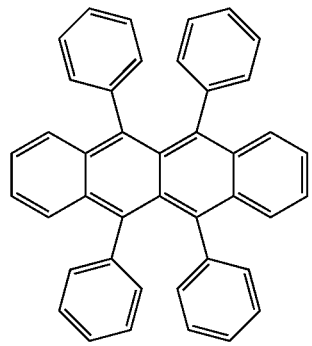

G3

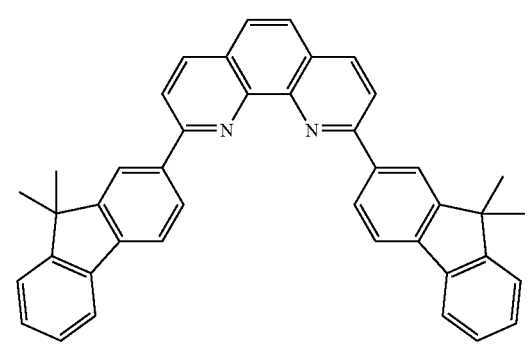

G4

In the organic light emitting element thus obtained, when the ITO electrode was used as a positive electrode, the Al electrode was used as a negative electrode, and a voltage was applied therebetween, red light emission having CIE chromaticity coordinates of (0.64, 0.35) and a light emitting efficiency of 12.9 cd/A at a voltage of 4.8 V was observed. In addition, when this organic light emitting element was driven at an initial luminance of 5,000 cd/m², the reduction rate in luminance was less than 10% even after 100 hours passed.

Example 14

Except that the compound (C1) for the guest was changed to the compound (B1), an organic light emitting element was formed in a manner similar to that of Example 13.

In the organic light emitting element thus obtained, when the ITO electrode was used as a positive electrode, the Al electrode was used as a negative electrode, and a voltage was applied therebetween, red light emission having CIE chromaticity coordinates of (0.65, 0.34) and a light emitting efficiency of 10.7 cd/A at a voltage of 4.0 V was observed. In addition, when this organic light emitting element was driven at an initial luminance of 5,000 cd/m², the reduction rate in luminance was less than 10% even after 100 hours passed.

Example 15

Except that the compound (C1) for the guest was changed to the compound (A6), an organic light emitting element was formed in a manner similar to that of Example 13.

In the organic light emitting element thus obtained, when the ITO electrode was used as a positive electrode, the Al electrode was used as a negative electrode, and a voltage was applied therebetween, red light emission having CIE chromaticity coordinates of (0.64, 0.35) and a light emitting efficiency of 13.5 cd/A at a voltage of 4.7 V was observed. In addition, when this organic light emitting element was driven at an initial luminance of 5,000 cd/m², the reduction rate in luminance was less than 10% even after 100 hours passed.

Example 16

In this example, an organic white light emitting element having the structure in which an anode/hole injection layer/hole transport layer/blue light emitting layer/green light emitting layer/red light emitting layer/electron transport layer/electron injection layer/cathode were sequentially provided on a substrate was formed by the following method.

An ITO film having a thickness of 120 nm formed as an anode on a glass substrate by a sputtering method was used as a transparent conductive support substrate (ITO substrate). The following organic compound layers and electrode layers were successively formed on this ITO substrate using vacuum deposition performed by resistance heating in a vacuum chamber at a pressure of $10^{-5}$ Pa. In this case, the electrode surfaces facing each other were each formed to have an area of 3 mm².
Hole injection layer (30 nm) Compound (G1)
Hole transport layer (10 nm) Compound (G2)
Blue light emitting layer (10 nm) Host: Compound (G5) (Weight ratio: 95.0%), Guest: Compound (G6) (Weight ratio: 5.0%)
Green light emitting layer (10 nm) Host: Compound (G5) (Weight ratio: 95.0%), Guest: Compound (G7) (Weight ratio: 5.0%)
Red light emitting layer (10 nm) Host 1: Compound (G5) (Weight ratio: 39.5%), Host 2: Compound (G3) (Weight ratio: 60.0%), Guest: Compound (C1) (Weight ratio: 0.5%)
Electron transport layer (30 nm) Compound (G4)
Electron injection layer (1 nm) LiF
Metal electrode layer (100 nm) Al

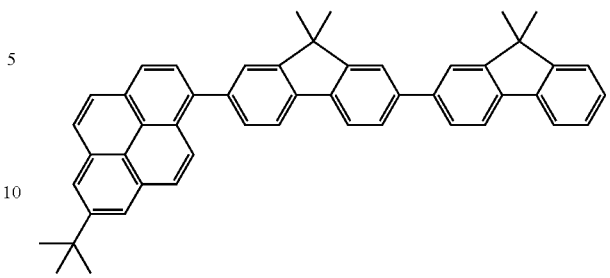

G5

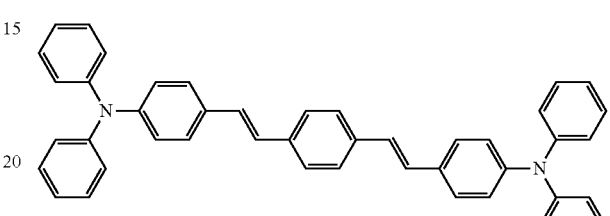

G6

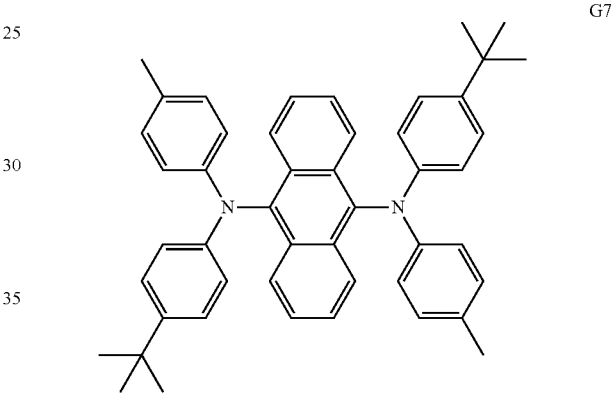

G7

In the organic light emitting element thus obtained, when the ITO electrode was used as a positive electrode, the Al electrode was used as a negative electrode, and a voltage was applied therebetween, white light emission having CIE chromaticity coordinates of (0.34, 0.35) was observed.

Example 17

Except that the compound (C1) for the guest was changed to the compound (B1), an organic light emitting element was formed in a manner similar to that of Example 16.

In the organic light emitting element thus obtained, when the ITO electrode was used as a positive electrode, the Al electrode was used as a negative electrode, and a voltage was applied therebetween, white light emission having CIE chromaticity coordinates of (0.34, 0.34) was observed.

As has thus been described, the novel condensed polycyclic compound according to aspects of the present invention exhibits red light emission, and an organic red light emitting element having a high efficiency and a high color purity can be provided.

In addition, when the condensed polycyclic compound according to aspects of the present invention is used in combination with at least one light emitting material which emits different color light, a white light emitting element can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-187169 filed Aug. 30, 2011, which is hereby incorporated by reference herein in its entirety.

What is claimed is:

1. An organic compound represented by the following general formula [1]

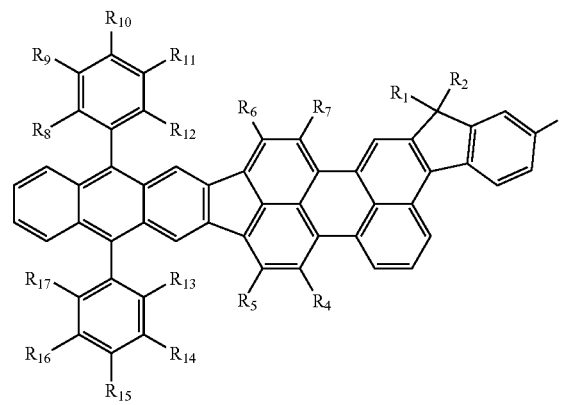

[1]

wherein in the general formula [1], $R_1$ to $R_3$ are each independently selected from the group consisting of a hydrogen atom, a fluorine group, an alkyl group having 1 to 4 carbon atoms, and an aryl group, the aryl group is a phenyl group, a biphenyl group, or a terphenyl group, the aryl group may further include an alkyl group having 1 to 4 carbon atoms and/or a fluorine group as a substituent, $R_4$ to $R_{17}$ are each independently selected from the group consisting of a hydrogen atom, an alkyl group having 1 to 4 carbon atoms, and a fluorine group, $R_1$ and $R_2$ may be bonded to form a ring so that the organic compound is represented by the following general formula [2], and

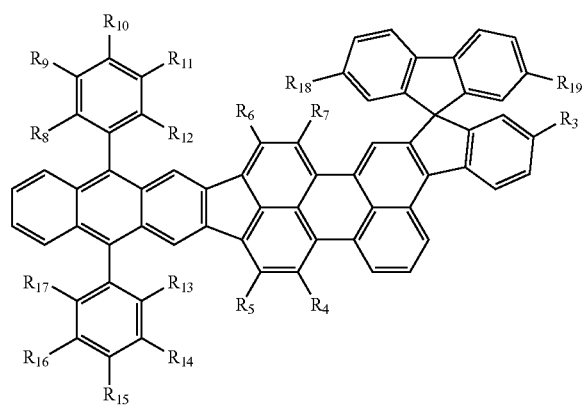

[2]

in the general formula [2], $R_{18}$ and $R_{19}$ are each independently selected from the group consisting of a hydrogen atom, a fluorine group, and a t-butyl group.

2. The organic compound according to claim 1, which is represented by the following general formula [3]

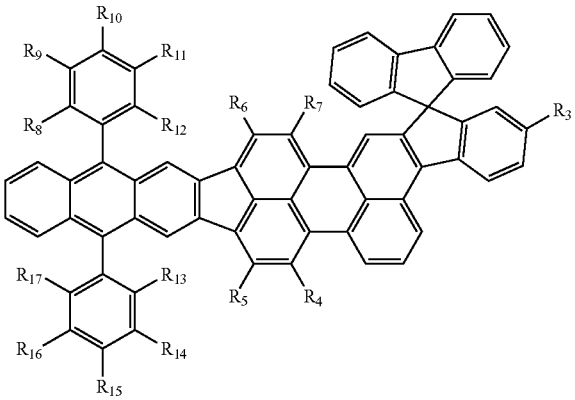

[3]

wherein in the general formula [3], $R_3$ is independently selected from the group consisting of a hydrogen atom, a fluorine group, an alkyl group having 1 to 4 carbon atoms, and an aryl group, the aryl group is a phenyl group, a biphenyl group, or a terphenyl group, the aryl group may further include an alkyl group having 1 to 4 carbon atoms and/or a fluorine group as a substituent, and $R_4$ to $R_{17}$ are each independently selected from the group consisting of a hydrogen atom, an alkyl group having 1 to 4 carbon atoms, and a fluorine group.

3. An organic light emitting element comprising:
a pair of electrodes; and
an organic compound layer arranged therebetween,
wherein the organic compound layer contains the organic compound according to claim 1.

4. The organic light emitting element according to claim 3, wherein the organic compound layer is a light emitting layer.

5. The organic light emitting element according to claim 4, which exhibits red light emission.

6. The organic light emitting element according to claim 4, wherein the light emitting layer includes a plurality of light emitting sublayers, and
at least one of the light emitting sublayers is a red light emitting sublayer so that the organic light emitting element emits white light.

7. The organic light emitting element according to claim 4, wherein the light emitting layer includes a blue, a green, and a red light emitting sublayer, and
the three light emitting sublayers each emit light.

8. A display device comprising:
a plurality of pixels,
wherein the pixels each include the organic light emitting element according to claim 3 and a switching element connected thereto.

9. An image output device comprising:
an input portion to input image information; and
a display portion to output an image,
wherein the display portion includes a plurality of pixels, and the pixels each include the organic light emitting element according to claim 3 and a switching element connected thereto.

10. A lighting device comprising:

the organic light emitting element according to claim 3; and an inverter to apply a direct current voltage to the organic light emitting element.

11. The lighting device according to claim 10, which exhibits white light emission.

* * * * *